United States Patent
Prince et al.

(10) Patent No.: US 7,364,918 B2
(45) Date of Patent: *Apr. 29, 2008

(54) COLORIMETRIC SENSORS CONSTRUCTED OF DIACETYLENE MATERIALS

(75) Inventors: Ryan B. Prince, Woodbury, MN (US); David S. Hays, Woodbury, MN (US); Angela K. Dillow, Minneapolis, MN (US); Randall P. Brown, White Bear Township, MN (US); G. Marco Bommarito, Stillwater, MN (US); John L. Battiste, Northfield, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 210 days.

This patent is subject to a terminal disclaimer.

(21) Appl. No.: 10/738,573

(22) Filed: Dec. 16, 2003

(65) Prior Publication Data

US 2004/0132217 A1    Jul. 8, 2004

Related U.S. Application Data

(63) Continuation-in-part of application No. 10/325,801, filed on Dec. 19, 2002, now abandoned.

(51) Int. Cl.
| C12M 1/34 | (2006.01) |
| G01N 33/53 | (2006.01) |
| G01N 33/566 | (2006.01) |
| G01N 33/544 | (2006.01) |
| G01N 33/545 | (2006.01) |
| C07C 57/24 | (2006.01) |
| C07C 57/22 | (2006.01) |

(52) U.S. Cl. .......... 436/287.2; 436/501; 436/528; 436/531; 436/164; 435/7.1; 435/7.8; 530/812; 558/333

(58) Field of Classification Search .......... 436/501, 436/528, 531, 527, 164, 287.2; 435/7.1, 435/7.8; 530/812; 558/333
See application file for complete search history.

(56) References Cited

U.S. PATENT DOCUMENTS

| | | | |
|---|---|---|---|
| 3,709,860 A | 1/1973 | Fischer et al. | 260/77.5 |
| 3,999,946 A | 12/1976 | Patel et al. | 23/253 |
| 4,189,399 A | 2/1980 | Patel | 252/408 |
| 4,195,058 A | 3/1980 | Patel | 422/56 |
| 4,215,208 A | 7/1980 | Yee et al. | 526/285 |
| 4,228,126 A | 10/1980 | Patel et al. | 422/56 |
| 4,235,108 A | 11/1980 | Patel | 73/356 |
| 4,238,352 A | 12/1980 | Patel | 252/408 |
| 4,299,917 A | 11/1981 | Berger et al. | 435/19 |
| 4,339,240 A | 7/1982 | Patel | 23/230 |
| 4,389,217 A | 6/1983 | Baughman et al. | 436/2 |
| 4,434,235 A | 2/1984 | Rabi et al. | 436/110 |
| 4,721,769 A | 1/1988 | Rubner | 528/75 |
| 4,735,745 A | 4/1988 | Preziosi et al. | 252/408 |
| 4,767,826 A | 8/1988 | Liang et al. | 525/421 |
| 4,849,500 A | 7/1989 | Rubner | 528/345 |
| 4,916,211 A | 4/1990 | Rubner | 528/480 |
| 5,156,810 A | 10/1992 | Ribi | 422/82 |
| 5,491,097 A | 2/1996 | Ribi et al. | 436/518 |
| 5,571,568 A | 11/1996 | Ribi et al. | 427/487 |
| 5,618,735 A | 4/1997 | Saul et al. | 436/518 |
| 5,622,872 A | 4/1997 | Ribi | 436/518 |
| 5,660,993 A | 8/1997 | Cathey et al. | 435/7.9 |
| 5,672,465 A | 9/1997 | Patel et al. | 430/332 |
| 5,685,641 A | 11/1997 | Ribi | 374/162 |
| 5,753,517 A | 5/1998 | Brooks et al. | |
| 5,798,215 A | 8/1998 | Cathey et al. | 435/7.9 |
| 5,918,981 A | 7/1999 | Ribi | 374/162 |
| 5,951,993 A | 9/1999 | Scholz et al. | |
| 6,046,455 A | 4/2000 | Ribi et al. | 250/372 |
| 6,080,423 A | 6/2000 | Charych et al. | 424/450 |
| 6,103,217 A | 8/2000 | Charych | 424/321 |
| 6,156,524 A | 12/2000 | Fournier et al. | 435/7.33 |
| 6,183,772 B1 | 2/2001 | Charych et al. | 424/450 |
| 6,277,652 B1 | 8/2001 | Jo et al. | 436/518 |
| 6,299,897 B1 | 10/2001 | Nagy et al. | 424/443 |
| 6,306,598 B1 | 10/2001 | Charych et al. | 435/6 |
| 6,361,962 B1 | 3/2002 | Lentini et al. | 435/29 |
| 6,375,871 B1 | 4/2002 | Bentsen et al. | 264/1.6 |

(Continued)

FOREIGN PATENT DOCUMENTS

EP    0 532 430 A1    7/1992

(Continued)

OTHER PUBLICATIONS

Alekseev et al. Polymerization of a diacetylenic alcohol and its mixtures with a diacetylenic acid in langmuir-blodgett films. Russian Journal of Physical Chemistry 2002, vol. 76, No. 5, pp. 796-801.*
Charych et al., A 'litmus test' for molecular recognition using artificial membranes. Current Biology 1996, vol. 3, pp. 113-120.*
STN search of p. 1 and 2. Alekseev et al. Document No. 137:248029, Russian Journal of Physical Chemistry. Abstract of U document cited in U of 892.*
Pan et al. "Molecular Recognition and Colorimetric Detection of Cholera Toxin in Poly(diacetylene) Liposomes Incorporating $G_{m1}$ Ganglioside"; Langmuir 1997, 13, pp. 1365-1367 (1997 American Chemical Society).

(Continued)

*Primary Examiner*—Long V. Le
*Assistant Examiner*—Shafiqul Haq
(74) *Attorney, Agent, or Firm*—Nancy M. Lambert

(57) ABSTRACT

Colorimetric sensors comprising a receptor incorporated within polydiacetylene assemblies to form a transducer capable of indicating a color change when contacted with an analyte are disclosed. Methods of using the colorimetric sensor and a kit for the colorimetric detection of an analyte are also disclosed.

32 Claims, 3 Drawing Sheets

U.S. PATENT DOCUMENTS

| | | | |
|---|---|---|---|
| 6,387,614 B1 | 5/2002 | Cheng et al. ................ 435/4 |
| 6,395,561 B1* | 5/2002 | Charych et al. ............ 436/501 |
| 6,420,622 B1 | 7/2002 | Johnston et al. .............. 602/41 |
| 6,451,191 B1 | 9/2002 | Bentsen et al. ............. 204/600 |
| 6,607,744 B1 | 8/2003 | Ribi .......................... 424/439 |
| 6,963,007 B2* | 11/2005 | Hays et al. ................. 558/333 |
| 2001/0046451 A1 | 11/2001 | Patel ........................... 422/58 |
| 2002/0137233 A1 | 9/2002 | Stevens et al. ............. 436/531 |
| 2004/0126897 A1 | 7/2004 | Prince et al. ............... 436/518 |
| 2004/0132217 A1 | 7/2004 | Prince et al. ............... 436/518 |
| 2005/0101794 A1 | 5/2005 | Hays et al. |
| 2005/0153370 A1 | 7/2005 | Lakshmi et al. |
| 2006/0041057 A1 | 2/2006 | Koecher et al. ............. 525/50 |
| 2006/0041099 A1 | 2/2006 | Cernohous et al. .......... 528/44 |
| 2006/0134796 A1 | 6/2006 | Bommarito et al. ........ 436/166 |

FOREIGN PATENT DOCUMENTS

| | | |
|---|---|---|
| EP | 0 926 497 A2 | 6/1999 |
| GB | 1 361 577 | 7/1974 |
| GB | 1 463 434 | 2/1977 |
| JP | 4-69358 | 3/1992 |
| JP | 11-28099 | 2/1999 |
| WO | WO 96/21885 | 7/1996 |
| WO | WO 99/10743 A1 | 3/1999 |
| WO | WO 01/71317 A1 | 9/2001 |
| WO | WO 02/00920 A2 | 1/2002 |
| WO | WO 02/079486 | 10/2002 |
| WO | WO 02/082086 | 10/2002 |

OTHER PUBLICATIONS

Ma et al. "Colorimetric Detection of *Escherichia coli* by Polydiacetylene Vesicles Functionalized with Glycolipid"; J. Am. Chem. Soc. 1998, 120; pp. 12678-12679 (1998 American Chemical Society).

Mino et al.; "Photoreactivity of 10,12-Pentacosadiynoic Acid Monolayrs and Color Transitions of the Polymerized Monolayers on an Aqueous Subphase"; Langmuir, 1992, vol. 8, 594-598.

Chance et al.; "Thermal effects on the optical properties of single crystals and solution-cast films of urethane substituted polydiacetylenes"; J. Chem. Phys.; vol. 71(1) Jul. 1, 1979; pp. 206-211.

Shibata, M.; "Reversible Colour Phase Transitions and Annealing Properties of Langmuir-Blodgett Polydiacetylene Films"; Thin Solid Films; vol. 179 (1989) pp. 433-437.

Kaneko et al.; "Absorption properties and structure changes caused by pre-annealing in polydiacetylene Langmuir-Blodgett films"; Thin Solid Films; vol. 210/211 (1992) pp. 548-550.

A. Ulman; "An Introduction to Ultrathin Organic Films" 1991 pp. 237-304.

A. Ulman; "An Introduction to Ultrathin Organic Films" 1991 pp. 101-236.

A. Ulman; "An Introduction to Ultrathin Organic Films" 1991 pp. 48-58.

Abrams et al.; "Triple Bond Isomerizations: 2- to 9-Decyn-1-o1"; Organic Syntheses; vol. 66, 1988 pp. 127-131.

Brandsma, L.; Preparative Acetylenic Chemistry; 1971 (cover and copyrights pages).

Alcaraz et al.; "Synthesis and Properties of Photoactivatable Phospholipid Derivatives Designed to Probe the Membrane-Associate Domains of Proteins"; J. Org. Chem.; vol. 61; 1996 pp. 192-201.

Wu, S.; "Polymer Interface and Adhesion" 1982; pp. 169-198, 613-618.

Millar et al; "Synthesis of Z,Z-Skipped Diene Macrolide Pheromones for Cryptolestes and Oryzaephilus Grain Beetles (*Coleoptera cucujidae*)" J. Org. Chem.; vol. 49, 1984; pp. 2332-2338.

Mohanty et al.; "A highly sensitive fluorescent micro-assay of $H_2O_2$ release from activated human leukocytes using a dihydroxyphenoxazine derivative"; Journal of Immunological Methods; vol. 202 (1997) pp. 133-141.

Kolusheva et al.; "A colorimetric assay for rapid screening of antimicrobial peptides"; Nature Biotechnology; vol. 18, Feb. 2000 pp. 225-227.

Kolusheva et al.; "Rapid Colorimetric Detection of Antibody-Epitope Recognition at a Biomimetic Membrane Interface"; J. Am. Chem. Soc.; vol. 123; 2001; pp. 417-422.

Kolusheva et al.; "Peptide-Membrane Interactions Studied by a New Phospholipid/Polydiacetylene Colorimetric Vesicle Assay"; Biochemistry; vol. 39; 2000; pp. 15851-15859.

Koshkina et al.; "Synthesis of New Amphiphilic Bifunctional Diynes Modified in the Hydrophilic and Hydrophobic Parts*"; Russian Journal of Organic Chemistry; vol. 30; No. 9; 1994; pp. 1345-1351.

Xu et al.; "Synthesis of Photopolymerizable Long-Chain Conjugated Diacetylenic Acids and Alcohols from Butadiyne Synthons"; J. Org. Chem.; vol. 56; 1991; pp. 7183-7186.

Bell et al; "The total synthesis of a technetium chelate—tamoxifen complex"; Can. J. Chem. vol. 77; 1999; pp. 146-154.

Bader et al.; "Membrane-spanning Symmetric and Asymmetric Diyne Amphiphiles"; Faraday Discuss. Chem. Soc.; vol. 81; 1986; pp. 329-337.

Ohba et al.; "Synthesis of Novel Amphiphilic Diacetylenes with Amino or Ammonium Functionality"; Tetrahedron, vol. 47, No. 47, pp. 9947-9952, 1991.

Alami et al.; A Convenient Route to Unsymmetrical Conjugated Diynes; Tetrahedron Letters, vol. 37, No. 16, pp. 2763-2766, 1996.

Baughman, R.H. et al.; "Raman spectral shifts relevant to electron delocalization in polydiacetylenes"; The Journal of Chemical Physics; vol. 60, No. 12, Jun. 15, 1974; pp. 4755-4759.

Dumont, J. et al.; "Amines et aminoacides polyacetyleniques"; C.R. Acad. Sc. Paris, t 260 (Jan. 4, 1965). Groupe 8. pp. 215-217 (no translation sent).

Dumont, J. et al.; "Contribution a l'etude des amines ω-acetyleniques vrais et de leurs derives"; Bulletin De La Societe Chimique De France 1967 No. 2; pp. 588-596 (no translation sent).

Kosuge, H. et al.; "Polydiacetylenes in Organic-Inorganic Hybrid Systems"; Mol. Cryst. Liq. Cryst., vol. 377, pp. 13-18 2002.

Budilova, I. et al.; "Reaction of Diynoyl Chlorides with Para-Substituted Phenols"; J. Org. Chem. USSR. vol. 26; 1990; pp. 264-267.

Gusev B.P. et al.; "Chemistry of Polyenic and Polyacetylenic Compounds Communication 6. New Method for the Synthesis of Butadiyne Derivatives"; Bull. Acad. Sci. USSR Div. Chem. Sci. 1962; pp. 1000-1005.

Besace, Y. et al.; "Reaction de Delepine en serie acetylenique"; Bulletin De La Societe Chimique De France; 1971, No. 4; pp. 1468-1472 (no translation sent).

Besace, Y. et al.; "Synthese des amines primaries α-diacetyleniques par la methode de Delepine"; C.R. Acad. Sc. Paris, t.270 (May 11, 1970); pp. 1605-1607 (no translation sent).

Rodriguez-Abad, R. et al.; "Unsymmetrically Substituted Aliphatic Diacetylenes Containing Amine Functionalities"; Synthetic Communications, 28(23), pp. 4333-4338 (1998).

Gusev, B.P. et al.; "Chemistry of Polyenic and Polyynic Compounds Communication 13. Synthesis of Dialkylamino Derivatives of 1,3-Diynes"; Bull. Acad. Sci. USSR Div. Chem. Sci.; 1965; pp. 820-823.

Gusev, B.P. et al.; "Chemistry of Polyenic and Polyynic Compounds Communication 18. Diacetylenic Amines"; Bull. Acad. Sci. USSR Div. Chem. Sci.; 1996; pp 1163-1166.

Singh, A. et al.; "Self-assembled Microstructures from a Polymerizable Ammonium Surfactant: Di(Hexacosa-12,14-diynyl)dimethylammonium Bromide"; J. Chem. Soc. Chem. Commun., 1988; pp. 1222-1223.

Schulze, K. et al.; "Zum Mechanismus Der Umlagerung Beim Alkalischen Abbau Der Quartaren Salze Von 1-Dialkylaminoalkadinen-(2,4)"; Tetrahedron, vol. 31, pp. 1455-1459; 1975 (no translation sent).

Cannon, J. et al.; "1,6-Diammonium-2,4-hexadiyne Analogs of Hexamethonium"; Journal of Medicinal Chemistry, 1974, vol. 17, No. 3, pp. 355-358.

Khoobehi, B. et al.; "Fluorescent Labeling of Blood Cells for Evaluation of Retinal and Choroidal Circulation"; Ophthalmic Surgery and Lasers; vol. 30; No. 2; Feb. 1999 pp. 140-145.

Hupfer, B et al.; "Spreading and Polymerization Behavior of Diacetylenic Phospholipids at the Gas-Water Interface"; Chemistry and Physics of Lipids; vol. 33; 1983; pp. 263-282.

J. Israelachvili; "Intermolecular and Surface Forces" (2nd Ed.); Academic Press, New York (1992) pp. 340-435.

Rubner, M.F.; "Synthesis and Characterization of Polyurethane-Diacetylene Segmented Copolymers"; Macromolecules 1986, vol. 19, p. 2114-2128.

Rubner, M.F.; "Novel Optical Properties of Polyurethane-Diacetylene Segmented Copolymers"; Macromolecules 1986; vol. 19, p. 2129-2138.

Nallicheri, R.A. et al.; "Thermal and Mechanical Properties of Polyurethane-Diacetylene Segmented Copolymers. 1. Molecular Weight and Annealing Effects"; Macromolecules 1990; vol. 23, p. 1005-1016.

Nallicheri, R.A. et al.; "Thermal and Mechanical Properties of Polyurethane-Diacetylene Segmented Copolymers. 2. Effects of Diacetylene Cross-Polymerization"; Macromolecules 1990; vol. 23, p. 1017-1025.

Hammond, P.T. et al.; "Thermochromism in Liquid Crystaline Polydiacetylenes"; Macromolecules 1997; vol. 30, p. 5773-5782.

Siemsen, P. et al.; "Acetylenic Coupling: A Powerful Tool in Molecular Construction"; Angewandte Chemie International Edition; 2000; vol. 39 (15); p. 2632-2657.

Andersson, K, et al.; "Predicting the kinetics of peptide-antibody interactions using a multivariate experimental design of sequence and chemical space"; Journal of Molecular Recognition; 2001; vol. 14, pp. 62-71.

Cheng, Q. et al.; "Amino Acid Terminated Polydiacetylene Lipid Microstructures: Morphology and Chromatic Transition"; Langmuir; 2000, vol. 16, pp. 5333-5342.

Valverde, C.; "Some Novel Photosensitive Diacetylene Diurethanes and Their Mixtures in Common Polymers"; Polymers for Advanced Technologies; vol. 7, 1996; pp. 27-30.

M. Paulsson et al.; "Adhesion of *Staphylococci* to Chemically Modified and Native Polymers, and the Influence of Preadsorbed Fibronectin, Vitronectin and Fibrinogen"; *Biomaterials*; 1993, vol. 14, No. 11: pp. 845-853.

A. Warnes; Development of an enzyme-linked immunosorbent assay for staphylococcal protein A produced in *Escherichia coli* by pUC8 based plasmids containing the *Staphylococcus aureus* Cowan I protein A gene; Journal of Immunological Methods, 93 (1986); pp. 63-70.

D. Low; "Issues in Identification and Susceptibility Testing, The *staphylococci* in Human Disease"; Clinical Microbiology; 1997; pp. 233-252.

J. Israelachvili et al.; "Physical principles of membrane organization"; Quarterly Reviews of Biophysics 13, 2 (1980) pp. 121-200.

M. Starzak; The Physical Chemistry of Membranes; Department of Chemistry; 1984; pp. 1-24.

S. Oellerich et al.; "Peripheral and Integral Binding of Cytochrome c to Phospholipids Vesicles"; Journal of Physical Chemistry B.; 2004; 108; pp. 3871-1878.

M. Zuckermann et al.; "Insertion and Pore Formation Driven by Adsorption of Proteins Onto Lipid Bilayer Membrane-Wafer Interfaces"; Biophysical Journal; vol. 81; Nov. 2001; pp. 2458-2472

M. Shibata et al.; "Reversible Colour Phase Transitions and Annealing Properties of Langmuir-Blodgett Polydiacetylene Films"; Thin Solid Films; 179 (1989) pp. 433-437.

A. S. Alekseev et al.; "Polymerization of a Diacetylenic Alcohol and its Mixtures with a Diacetylenic Acid in Langmuir-Blodgett Films"; Russian Journal of Physical Chemistry, vol. 76, No. 5, 2002 pp. 796-801.

D. Charych et al.; "A Litmus Test for Molecular Recognition Using Artificial Membranes"; Current Biology Ltd.; Chemistry & Biology, Feb. 1996, 3: pp. 113-120.

* cited by examiner

COLORIMETRIC SENSORS CONSTRUCTED OF DIACETYLENE MATERIALS

CROSS REFERENCE TO RELATED APPLICATIONS

This application is a continuation-in-part of U.S. patent application Ser. No. 10/325,801, filed Dec. 19, 2002 now abandoned.

FIELD OF THE INVENTION

The present invention relates to a technique for detection of analytes using observable spectral changes in polydiacetylene assemblies. More specifically, this invention relates to a colorimetric sensor comprising polydiacetylene assemblies and a method of using the sensor to detect an analyte.

BACKGROUND OF THE INVENTION

Diacetylenes are typically colorless and undergo addition polymerization, either thermally or by actinic radiation. As the polymerization proceeds, these compounds undergo a contrasting color change to blue or purple. When exposed to external stimuli such as heat, physical stress or a change of solvents or counterions, polydiacetylenes exhibit a further color changes produced by distortion of the planar backbone conformation. Polydiacetylene assemblies are known to change color from blue to red with an increase in temperature or changes in pH due to conformational changes in the conjugated backbone as described in Mino, et al., Langmuir, Vol. 8, p. 594, 1992; Chance, et al., *Journal of Chemistry and Physics*, Vol. 71, 206, 1979; Shibutag, *Thin Solid Films*, Vol. 179, p. 433, 1989; Kaneko, et al., *Thin Solid Films*, Vol. 210, 548, 1992; and U.S. Pat. No. 5,672,465. Utilization of this class of compounds is known for use as biochromic indicators as discussed in U.S. Pat. No. 5,622,872 and publication WO 02/00920.

Proposed applications of polydiacetylenes for detection of analytes are discussed in U.S. Pat. Nos. 6,395,561 B1; 6,306,598 B1; 6,277,652; 6,183,772; 6,080,423 and publication WO 01/71317. In particular, attempts have been made to construct biosensors with receptors that react specifically with pathogenic bacteria, viruses, toxins and the like incorporated into polydiacetylene membranes, and the color change (blue to red) is induced when the receptors bind to their specific analytes (pathogenic bacteria, viruses, toxins, etc.) Such methods require that the binding structure of the receptor and analyte be known, and the receptor identified. Synthesis of both the receptors and the polydiacetylene membranes can be complicated and difficult. The polydiacetylene membranes can exhibit insufficient color change upon binding with an analyte, requiring other substances for promoting the structural change or enhancing analytical equipment to observe the color change.

SUMMARY OF THE INVENTION

A need continues to exist to make sensing devices employing diacetylenes more accurate, more tailored to a given application, less complex and more available to non-technical personnel in a wide variety of environments. Devices, which can be conveniently transported and used individually for a particular application then discarded, are particularly desirable.

The present invention provides a colorimetric sensor to detect the presence of analytes by spectral changes (color changes visible to the naked eye or with a colorimeter) that occur as a result of the specific binding of the analytes to polydiacetylene assemblies. The polydiacetylene assemblies indicate the presence of an analyte in a simple yet highly sensitive manner.

The present invention provides a colorimetric sensor comprising a receptor and the polymerization reaction product comprising at least one compound of the formula

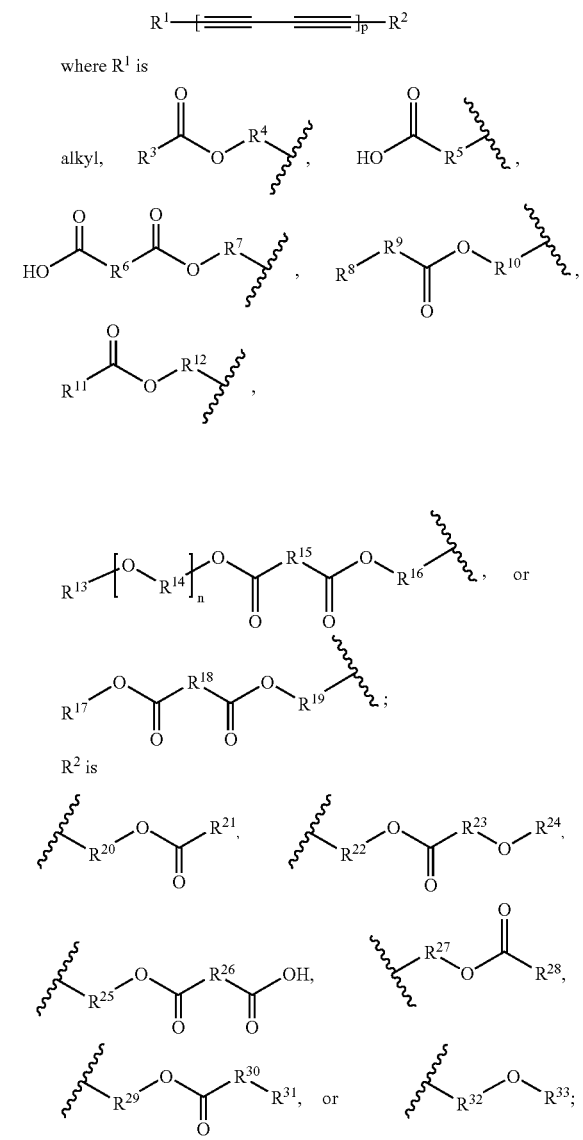

$R^3$, $R^8$, $R^{13}$, $R^{21}$, $R^{24}$, $R^{31}$ and $R^{33}$ are independently alkyl; $R^4$, $R^5$, $R^7$, $R^{14}$, $R^{16}$, $R^{19}$, $R^{20}$, $R^{22}$, $R^{25}$, and $R^{32}$ are independently alkylene; $R^6$, $R^{15}$, $R^{18}$, and $R^{26}$ are independently alkylene, alkenylene, or arylene; $R^9$ is alkylene or —$NR^{34}$—; $R^{10}$, $R^{12}$, $R^{27}$, and $R^{29}$ are independently alkylene or alkylene-arylene; $R^{11}$ and $R^{28}$ are independently alkynyl; $R^{17}$ is an ester-activating group; $R^{23}$ is arylene; $R^{30}$ is alkylene or —$NR^{36}$—; $R^{34}$, and $R^{36}$ are independently H or $C_1$-$C_4$ alkyl; p is 1-5; and n is 1-20; and where $R^1$ and $R^2$ are not the same.

Also provided is an easier preparation and use of polydiacetylene assemblies in solution and for deposition on a substrate.

Also provided is a device and method for the detection of small molecules, pathogenic and non-pathogenic organisms, toxins, membrane receptors and fragments, volatile organic compounds, enzymes and enzyme substrates, antibodies, antigens, proteins, peptides, nucleic acids, and peptide nucleic acids.

Also provided is a simple to use, inexpensive test kit whose reliability is relativity stable in a wide range of environmental conditions, and when the analyte is mixed with a number of other materials.

Also provided is a method for using the colorimetric sensor to detect an analyte by contacting the colorimetric sensor with an analyte and observing a color change.

Also provided is a method for indirect detection of an analyte by contacting the colorimetric sensor with a probe that has an affinity for both the analyte and the receptor, and observing no color change.

The above summary of the present invention is not intended to describe each disclosed embodiment or every implementation of the present invention. The detailed description that follows more particularly exemplifies these embodiments.

DETAILED DESCRIPTION

Figure 1:
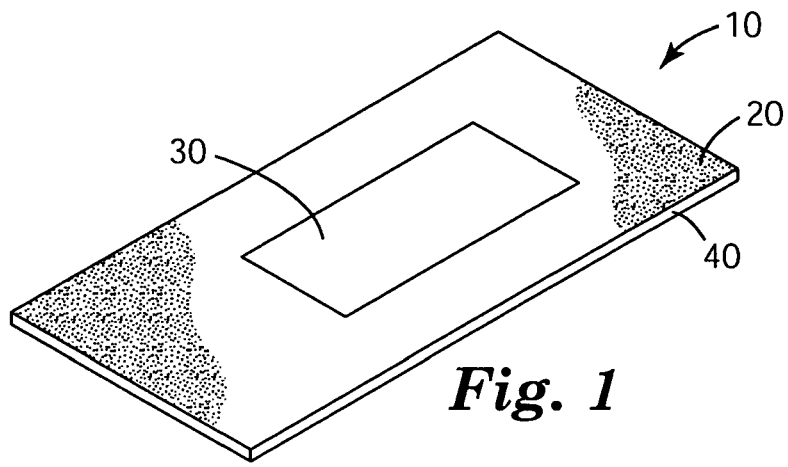
FIG. 1 shows a schematic representation of a colorimetric sensor of the present invention.

The present invention provides a colorimetic sensor comprising diacetylenic materials and a method of using the sensor to detect an analyte. While the present invention is not so limited, an appreciation of various aspects of the invention will be gained through a discussion of the examples provided below.

For the following defined terms, these definitions shall be applied, unless a different definition is given in the claims or elsewhere in this specification:

As used herein, the term "alkyl" refers to a straight or branched chain or cyclic monovalent hydrocarbon radical having a specified number of carbon atoms. Alkyl groups include those with one to twenty carbon atoms. Examples of "alkyl" as used herein include, but are not limited to, methyl, ethyl, n-propyl, n-butyl, n-pentyl, isobutyl, and isopropyl, and the like. It is to be understood that where cyclic moieties are intended, at least three carbons in said alkyl must be present. Such cyclic moieties include cyclopropyl, cyclobutyl, cyclopentyl, cyclohexyl and cycloheptyl.

As used herein, the term "alkylene" refers to a straight or branched chain or cyclic divalent hydrocarbon radical having a specified number of carbon atoms. Alkylene groups include those with one to fourteen carbon atoms. Examples of "alkylene" as used herein include, but are not limited to, methylene, ethylene, trimethylene, tetramethylene and the like. It is to be understood that where cyclic moieties are intended, at least three carbons in said alkylene must be present. Such cyclic moieties include cyclopropylene, cyclobutylene, cyclopentylene, cyclohexylene and cycloheptylene.

As used herein, the term "alkenylene" refers to a straight or branched chain or cyclic divalent hydrocarbon radical having a specified number of carbon atoms and one or more carbon—carbon double bonds. Alkenylene groups include those with two to eight carbon atoms. Examples of "alkenylene" as used herein include, but are not limited to, ethene-1,2-diyl, propene-1,3-diyl, and the like.

As used herein, the term "arylene" refers to divalent unsaturated aromatic carboxylic radicals having a single ring, such as phenylene, or multiple condensed rings, such as naphthylene or anthrylene. Arylene groups include those with six to thirteen carbon atoms. Examples of "arylene" as used herein include, but are not limited to, benzene-1,2-diyl, benzene-1,3-diyl, benzene-1,4-diyl, naphthalene-1,8-diyl, and the like.

As used herein, the term "alkylene-arylene", refers to an alkylene moiety as defined above bonded to an arylene moiety as defined above. Examples of "alkylene-arylene" as used herein include, but are not limited to, —$CH_2$-phenylene, —$CH_2CH_2$-phenylene, and —$CH_2CH_2CH_2$-phenylene.

As used herein, the term "alkynyl" refers to a straight or branched chain or cyclic monovalent hydrocarbon radical having from two to thirty carbons and at least one carbon-carbon triple bond. Examples of "alkynyl" as used herein include, but are not limited to, ethynyl, propynyl and butynyl.

As used herein, the term "analyte(s)" refers to any material that can be detected by the sensor of the present invention. Such materials include, but are not limited to small molecules, pathogenic and non-pathogenic organisms, toxins, membrane receptors and fragments, volatile organic compounds, enzymes and enzyme substrates, antibodies, antigens, proteins, peptides, nucleic acids, and peptide nucleic acids.

As used herein, the term "bacteria" refers to all forms of microorganisms considered to be bacteria including cocci, bacilli, spirochetes, sheroplasts, protoplasts, etc.

As used herein, the term "receptor" refers to any molecule with a binding affinity for an analyte of interest. Receptor includes, but is not limited to, naturally occurring receptors such as surface membrane proteins, enzymes, lectins, antibodies, recombinant proteins, etc.; synthetic proteins; nucleic acids; c-glycosides; carbohydrates; gangliosides; and chelating agents.

As used herein, the terms "assembly", or "self-assembly", refers to any self-ordering of diacetylene molecules prior to polymerization. J. Israelachvili, *Intermolecular and Surface Forces* ($2^{nd}$ Ed.), *Part Three—Fluid-Like Structures and Self-Assembling Systems: Micelles, Bilavers and Biological Membranes*: Academic Press, New York (1992), pp. 340-435.

As used herein, the term "self-assembling monolayer(s)" (SAMs) refers to any ordered ultrathin organic film formed on a given substrate by spontaneous self-ordering. A. Ulman, *An Introduction to Ultrathin Organic Films*, Academic Press, New York (1991), pp. 237-301.

As used herein, the term "transducer" describes a material capable of turning a recognition event at the molecular level into an observable signal.

All numbers are herein assumed to be modified by the term "about." The recitation of numerical ranges by endpoints includes all numbers subsumed within that range (e.g. 1 to 5 includes 1, 1.5, 2, 2.75, 3, 3.80, 4, and 5).

The present invention provides a colorimetric sensor comprising novel polydiacetylene assemblies incorporated with a receptor for detection of an analyte. The polydiacetylene assemblies are polymerized compounds of the formula

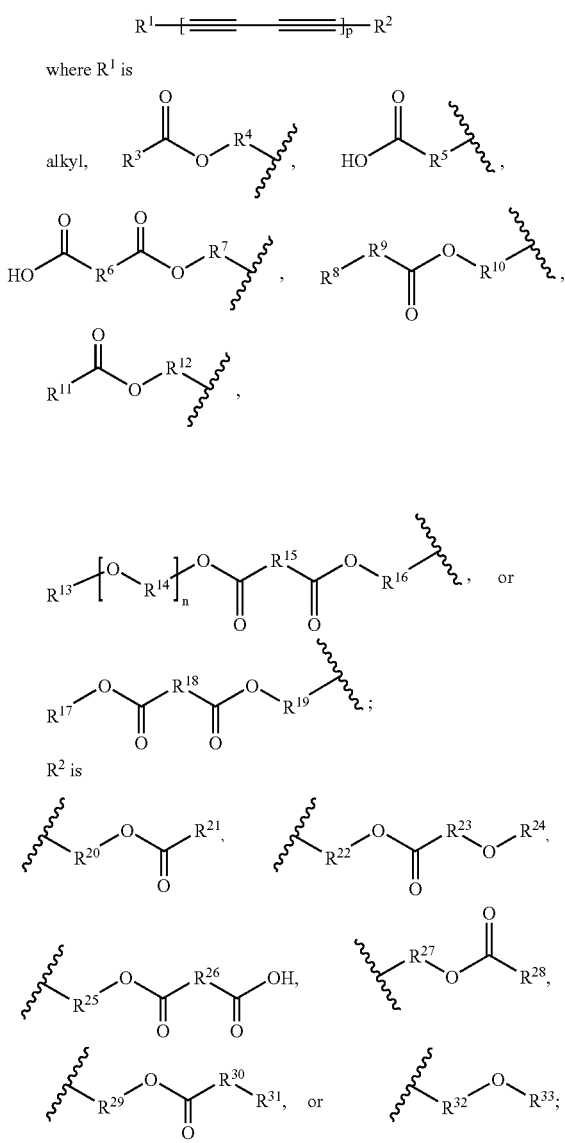

$R^3$, $R^8$, $R^{13}$, $R^{21}$, $R^{24}$, $R^{31}$ and $R^{33}$ are independently alkyl; $R^4$, $R^5$, $R^7$, $R^{14}$, $R^{16}$, $R^{19}$, $R^{20}$, $R^{22}$, $R^{25}$, and $R^{32}$ are independently alkylene; $R^6$, $R^{15}$, $R^{18}$, and $R^{26}$ are independently alkylene, alkenylene, or arylene; $R^9$ is alkylene or $-NR^{34}-$; $R^{10}$, $R^{12}$, $R^{27}$, and $R^{29}$ are independently alkylene or alkylene-arylene; $R^{11}$ and $R^{28}$ are independently alkynyl; $R^{17}$ is an ester-activating group; $R^{23}$ is arylene; $R^{30}$ is alkylene or $-NR^{36}-$; $R^{34}$, and $R^{36}$ are independently H or $C_1$-$C_4$ alkyl; p is 1-5; and n is 1-20; and where $R^1$ and $R^2$ are not the same.

Examples of $R^1$ when $R^1$ is alkyl include $C_1$-$C_{20}$ alkyl, $C_6$-$C_{18}$ alkyl, and $C_{12}$-$C_{16}$ alkyl. Additional examples of $R^1$ when $R^1$ is alkyl include dodecyl and hexadecyl.

Examples of $R^3$ include $C_1$-$C_{20}$ alkyl, and $C_6$-$C_{18}$ alkyl. Additional examples of $R^3$ include undecyl and pentadecyl.

Examples of $R^4$ include $C_1$-$C_{14}$ alkylene, and $C_1$-$C_4$ alkylene. Additional examples of $R^4$ include methylene ($-CH_2-$), trimethylene ($-CH_2CH_2CH_2-$), and tetramethylene ($-CH_2CH_2CH_2CH_2-$).

Examples of $R^5$ include $C_1$-$C_{14}$ alkylene, and $C_1$-$C_3$ alkylene. Additional examples of $R^5$ include ethylene ($-CH_2CH_2-$), and trimethylene ($-CH_2CH_2CH_2-$).

Examples of $R^6$ when $R^6$ is alkylene include $C_1$-$C_{14}$ alkylene, and $C_1$-$C_3$ alkylene. Additional examples of $R^6$ when $R^6$ is alkylene include ethylene ($-CH_2CH_2-$), and trimethylene ($-CH_2CH_2CH_2-$). Examples of $R^6$ when $R^6$ is alkenylene include $C_2$-$C_8$ alkenylene, and $C_2$-$C_4$ alkenylene. An additional example of $R^6$ when $R^6$ is alkenylene includes ethenylene ($-C=C-$). Examples of $R^6$ when $R^6$ is arylene include $C_6$-$C_{13}$ arylene, and phenylene. An additional example of $R^6$ when $R^6$ is arylene is benzene-1,2-diyl.

Examples of $R^7$ include $C_1$-$C_{14}$ alkylene, and $C_2$-$C_9$ alkylene. Additional examples of $R^7$ include ethylene ($-CH_2CH_2-$), trimethylene ($-CH_2CH_2CH_2-$), tetramethylene ($-CH_2CH_2CH_2CH_2-$), pentamethylene ($-CH_2CH_2CH_2CH_2CH_2-$), hexamethylene ($-CH_2CH_2CH_2CH_2CH_2CH_2-$), heptamethylene ($-CH_2CH_2CH_2CH_2CH_2CH_2CH_2-$), octamethylene ($-CH_2CH_2CH_2CH_2CH_2CH_2CH_2CH_2-$), and nonamethylene ($-CH_2CH_2CH_2CH_2CH_2CH_2CH_2CH_2CH_2-$).

Examples of $R^8$ include $C_1$-$C_{16}$ alkyl, and $C_1$-$C_8$ alkyl. Additional examples of $R^8$ include butyl, pentyl and hexyl.

$R^9$ is independently alkylene or $-NR^{34}-$, where $R^{34}$ is H or $C_1$-$C_{14}$ alkyl;

Examples of $R^9$ when $R^9$ is alkylene include $C_1$-$C_{14}$ alkylene, and $C_1$-$C_3$ alkylene, such as methylene ($-CH_2-$) for example. Examples of $R^9$ when $R^9$ is $-NR^{34}-$ include $-NH-$, $-N(CH_2CH_3)-$, and $-N(CH_3)-$.

Examples of $R^{10}$ when $R^{10}$ is alkylene include $C_1$-$C_{14}$ alkylene, and $C_1$-$C_8$ alkylene. Additional examples of $R^{10}$ when $R^{10}$ is alkylene include methylene ($-CH_2-$), ethylene ($-CH_2CH_2-$), trimethylene ($-CH_2CH_2CH_2-$), tetramethylene ($-CH_2CH_2CH_2CH_2-$), $-C(CH_3)_2-$, and $-CH((CH_2)_{1-4}CH_3)-$. Examples of $R^{10}$ when $R^{10}$ is alkylene-arylene include ($C_1$-$C_{14}$ alkylene)-arylene, and ($C_1$-$C_{14}$ alkylene)-phenylene. An additional example of $R_{10}$ when $R_{10}$ is alkylene-arylene includes $-CH_2$-phenylene.

Examples of $R^{11}$ include $C_2$-$C_{30}$ alkynyl, and $C_{20}$-$C_{25}$ alkynyl. Additional examples of $R^{11}$ include $C_2$-$C_{30}$ alkynyl having at least two carbon-carbon triple bonds ($-C\equiv C-$), and $C_{20}$-$C_{25}$ alkynyl having at least two carbon-carbon triple bonds. Further examples of $R^{11}$ include $C_{22}$ alkynyl having at least two carbon-carbon triple bonds, $C_{24}$ alkynyl having at least two carbon-carbon triple bonds. Yet further examples of $R^{11}$ include $-(CH_2)_8-C\equiv C-C\equiv C-(CH_2)_9CH_3$, and $-(CH_2)_8-C\equiv C-C\equiv C-(CH_2)_{11}CH_3$.

Examples of $R^{12}$ when $R^{12}$ is alkylene include $C_1$-$C_{14}$ alkylene, and $C_1$-$C_8$ alkylene. Additional examples of $R^{12}$ when $R^{12}$ is alkylene include methylene ($-CH_2-$), ethylene ($-CH_2CH_2-$), trimethylene ($-CH_2CH_2CH_2-$), tetramethylene ($-CH_2CH_2 CH_2CH_2-$), $-C(CH_3)_2-$, and $-CH((CH_2)_{1-4}CH_3)-$. Examples of $R^{12}$ when $R^{12}$ is alkylene-arylene include ($C_1$-$C_{14}$ alkylene)-arylene, and ($C_1$-$C_{14}$ alkylene)-phenylene. An additional example of $R^{12}$ when $R^{12}$ is alkylene-arylene includes —$CH_2$-phenylene.

Examples of $R^{13}$ include $C_1$-$C_4$ alkyl, such as methyl for example.

Examples of $R^{14}$ include $C_1$-$C_4$ alkylene, such as ethylene (—$CH_2CH_2$—) for example.

Examples of $R^{15}$ when $R^{15}$ is alkylene include $C_1$-$C_{14}$ alkylene, and $C_1$-$C_3$ alkylene. Additional examples of $R^{15}$ when $R^{15}$ is alkylene include ethylene (—$CH_2CH_2$—), and trimethylene (—$CH_2CH_2CH_2$—). Examples of $R^{15}$ when $R^{15}$ is alkenylene include $C_2$-$C_8$ alkenylene, and $C_2$-$C_4$ alkenylene. An additional example of $R^{15}$ when $R^{15}$ is alkenylene includes ethenylene (—C═C—). Examples of $R^{15}$ when $R^{15}$ is arylene include $C_6$-$C_{13}$ arylene, and phenylene. An additional example of $R^{15}$ when $R^{15}$ is arylene is benzene-1,4-diyl.

Examples of $R^{16}$ include $C_1$-$C_{14}$ alkylene, and $C_2$-$C_9$ alkylene. Additional examples of $R^{16}$ include ethylene (—$CH_2CH_2$—), trimethylene (—$CH_2CH_2CH_2$—), tetramethylene (—$CH_2CH_2CH_2CH_2$—), pentamethylene (—$CH_2CH_2CH_2CH_2CH_2$—), hexamethylene (—$CH_2CH_2CH_2CH_2CH_2CH_2$—), heptamethylene (—$CH_2CH_2CH_2CH_2CH_2CH_2CH_2$—), octamethylene (—$CH_2CH_2CH_2CH_2CH_2CH_2CH_2CH_2$—), and nonamethylene (—$CH_2CH_2CH_2CH_2CH_2CH_2CH_2CH_2CH_2$—).

Examples of $R^{17}$ include groups that activate the neighboring ester group toward acyl transfer. Such ester activating groups include pentafluorophenol, pentachlorophenol, 2,4,6-trichlorophenol, 3-nitrophenol, N-hydroxysuccinimide, N-hydroxyphthalimide and those disclosed in M. Bodanszky, "Principles of Peptide Synthesis," (Springer-Verlag 1984), for example. An additional example of $R^{17}$ is 2,5-dioxo-1-pyrrolidinyl.

Examples of $R^{18}$ when $R^{18}$ is alkylene include $C_1$-$C_{14}$ alkylene, and $C_1$-$C_3$ alkylene. Additional examples of $R^{18}$ when $R^{18}$ is alkylene include ethylene (—$CH_2CH_2$—), and trimethylene (—$CH_2CH_2CH_2$—). Examples of $R^{18}$ when $R^{18}$ is alkenylene include $C_2$-$C_8$ alkenylene, and $C_2$-$C_4$ alkenylene. An additional example of $R^{18}$ when $R^{18}$ is alkenylene includes ethenylene (—C═C—). Examples of $R^{18}$ when $R^{18}$ is arylene include $C_6$-$C_{13}$ arylene, and phenylene. An additional example of $R^{18}$ when $R^{18}$ is arylene is benzene-1,2-diyl.

Examples of $R^{19}$ include $C_1$-$C_{14}$ alkylene, and $C_2$-$C_9$ alkylene. Additional examples of $R^{19}$ include ethylene (—$CH_2CH_2$—), trimethylene (—$CH_2CH_2CH_2$—), tetramethylene (—$CH_2CH_2CH_2CH_2$—), pentamethylene (—$CH_2CH_2CH_2CH_2CH_2$—), hexamethylene (—$CH_2CH_2CH_2CH_2CH_2CH_2$—), heptamethylene (—$CH_2CH_2CH_2CH_2CH_2CH_2CH_2$—), octamethylene (—$CH_2CH_2CH_2CH_2CH_2CH_2CH_2CH_2$—), and nonamethylene (—$CH_2CH_2CH_2CH_2CH_2CH_2CH_2CH_2CH_2$—).

Examples of $R^{20}$ include $C_1$-$C_{14}$ alkylene, $C_1$-$C_9$ alkylene, and $C_1$-$C_4$ alkylene. Additional examples of $R^{20}$ include methylene (—$CH_2$—), ethylene (—$CH_2CH_2$—), trimethylene (—$CH_2CH_2CH_2$—), tetramethylene (—$CH_2CH_2CH_2CH_2$—), pentamethylene (—$CH_2CH_2CH_2CH_2CH_2$—), hexamethylene (—$CH_2CH_2CH_2CH_2CH_2CH_2$—), heptamethylene (—$CH_2CH_2CH_2CH_2CH_2CH_2CH_2$—), octamethylene (—$CH_2CH_2CH_2CH_2CH_2CH_2CH_2CH_2$—), and nonamethylene (—$CH_2CH_2CH_2CH_2CH_2CH_2CH_2CH_2CH_2$—).

Examples of $R^{21}$ when $R^{21}$ is alkyl include $C_1$-$C_{20}$ alkyl, $C_6$-$C_{18}$ alkyl, and $C_{10}$-$C_{17}$ alkyl. Additional examples of $R^{21}$ when $R^{21}$ is alkyl include decyl, undecyl, tridecyl, tetradecyl, pentadecyl, heptadecyl.

Examples of $R^{22}$ include $C_1$-$C_{14}$ alkylene, and $C_2$-$C_9$ alkylene. Additional examples of $R^{22}$ include ethylene (—$CH_2CH_2$—), trimethylene (—$CH_2CH_2CH_2$—), and tetramethylene.

Examples of $R^{23}$ include $C_6$-$C_{13}$ arylene, and phenylene. An additional example of $R^{23}$ when $R^{23}$ is arylene is benzene-1,4-diyl.

Examples of $R^{24}$ include $C_1$-$C_{20}$ alkyl, and $C_6$-$C_{18}$ alkyl. Additional examples of $R^{24}$ include methyl, ethyl, propyl, butyl, pentyl, hexyl, heptyl, octyl, nonyl, and dodecyl.

Examples of $R^{25}$ include $C_1$-$C_{14}$ alkylene, and $C_2$-$C_9$ alkylene. Additional examples of $R_{25}$ include ethylene (—$CH_2CH_2$—), trimethylene (—$CH_2CH_2CH_2$—), tetramethylene (—$CH_2CH_2CH_2CH_2$—), pentamethylene (—$CH_2CH_2CH_2CH_2CH_2$—), hexamethylene (—$CH_2CH_2CH_2CH_2CH_2CH_2$—), heptamethylene (—$CH_2CH_2CH_2CH_2CH_2CH_2$—), octamethylene (—$CH_2CH_2CH_2CH_2CH_2CH_2CH_2CH_2$—), and nonamethylene (—$CH_2CH_2CH_2CH_2CH_2CH_2CH_2CH_2CH_2$—).

Examples of $R^{26}$ when $R^{26}$ is alkylene include $C_1$-$C_{14}$ alkylene, and $C_1$-$C_3$ alkylene. Additional examples of $R^{26}$ when $R^{26}$ is alkylene include ethylene (—$CH_2CH_2$—), and trimethylene (—$CH_2CH_2CH_2$—). Examples of $R^{26}$ when $R^{26}$ is alkenylene include $C_2$-$C_8$ alkenylene, and $C_2$-$C_4$ alkenylene. An additional example of $R^{26}$ when $R^{26}$ is alkenylene includes ethenylene (—C═C—). Examples of $R^{26}$ when $R^{26}$ is arylene include $C_6$-$C_{13}$ arylene, and phenylene. An additional example of $R^{26}$ when $R^{26}$ is arylene is benzene-1,2-diyl.

Examples of $R^{27}$ when $R^{27}$ is alkylene include $C_1$-$C_{14}$ alkylene, and $C_1$-$C_8$ alkylene. Additional examples of $R^{27}$ when $R^{27}$ is alkylene include methylene (—$CH_2$—), ethylene (—$CH_2CH_2$—), trimethylene (—$CH_2CH_2CH_2$—), tetramethylene (—$CH_2CH_2$ $CH_2CH_2$—), —$C(CH_3)_2$—, and —$CH((CH_2)_{1-4}CH_3)$—. Examples of $R^{27}$ when $R^{27}$ is alkylene-arylene include ($C_1$-$C_{14}$ alkylene)-arylene, and ($C_1$-$C_{14}$ alkylene)-phenylene. An additional example of $R^{27}$ when $R^{27}$ is alkylene-arylene includes —$CH_2$-phenylene.

Examples of $R^{28}$ include $C_2$-$C_{30}$ alkynyl, and $C_{20}$-$C_{25}$ alkynyl. Additional examples of $R^{28}$ include $C_2$-$C_{30}$ alkynyl having at least two carbon-carbon triple bonds (—C≡C—), and $C_{20}$-$C_{25}$ alkynyl having at least two carbon-carbon triple bonds. Further examples of $R^{28}$ include $C_{22}$ alkynyl having at least two carbon-carbon triple bonds, $C_{24}$ alkynyl having at least two carbon-carbon triple bonds. Yet further examples of $R^{28}$ include —$(CH_2)_8$—C≡C—C≡C—$(CH_2)_9CH_3$, and —$(CH_2)_8$—C≡C—C≡C—$(CH_2)_{11}CH_3$.

Examples of $R^{29}$ when $R^{29}$ is alkylene include $C_1$-$C_{14}$ alkylene, and $C_1$-$C_8$ alkylene. Additional examples of $R^{29}$ when $R^{29}$ is alkylene include methylene (—$CH_2$—), ethylene (—$CH_2CH_2$—), trimethylene (—$CH_2CH_2CH_2$—), tetramethylene (—$CH_2CH_2$ $CH_2CH_2$—), —$C(CH_3)_2$—, and —$CH((CH_2)_{1-4}CH_3)$—. Examples of $R^{29}$ when $R^{29}$ is alkylene-arylene include ($C_1$-$C_{14}$ alkylene)-arylene, and ($C_1$-$C_{14}$ alkylene)-phenylene. An additional example of $R^{29}$ when $R^{29}$ is alkylene-arylene includes —$CH_2$-phenylene.

$R^{30}$ is independently alkylene or —$NR^{36}$—, where $R^{36}$ is H or $C_1$-$C_4$ alkyl;

Examples of $R^{30}$ when $R^{30}$ is alkylene include $C_1$-$C_{14}$ alkylene, and $C_1$-$C_3$ alkylene, such as methylene (—$CH_2$—) for example. Examples of $R^{30}$ when $R^{30}$ is —$NR^{36}$— include —NH—, —N($CH_2CH_3$)—, and —N($CH_3$)—.

Examples of $R^{31}$ include $C_1$-$C_{16}$ alkyl, and $C_1$-$C_8$ alkyl. Additional examples of $R^{31}$ include butyl, pentyl and hexyl.

Examples of $R^{32}$ include $C_1$-$C_{14}$ alkylene, and $C_2$-$C_9$ alkylene. Additional examples of $R^{32}$ include ethylene (—$CH_2CH_2$—), trimethylene (—$CH_2CH_2CH_2$—), tetramethylene (—CH$_2$CH$_2$CH$_2$CH$_2$—), pentamethylene (—CH$_2$CH$_2$CH$_2$CH$_2$CH$_2$—), and hexamethylene (—CH$_2$CH$_2$CH$_2$CH$_2$CH$_2$CH$_2$—).

Examples of R$^{33}$ include C$_1$-C$_{20}$ alkyl, C$_6$-C$_{18}$ alkyl, and C$_{10}$-C$_{16}$ alkyl. Additional examples of R$^{33}$ include dodecyl, tetradecyl, hexadecyl, and octadecyl.

Compounds of the present invention also include those where p can be 1 or 2 and n can be 1-20, 3-17, 6-14, or 9-11.

The invention is inclusive of the compounds described herein including isomers, such as structural isomers and geometric isomers, salts, solvates, polymorphs and the like.

Preparation of the Diacetylene Compounds

Diacetylenes of the Formula XXIII can be prepared as outlined in Scheme 1 where n is typically 1 to 4 and m is typically 10 to 14.

1 hour to 24 hours, generally 15 hours, at a temperature from 50° C. to 125° C., generally from 100° C. to 125° C.

The diacetylenic compounds as disclosed herein self assemble in solution to form ordered assemblies that can be polymerized using any actinic radiation such as, for example, electromagnetic radiation in the UV or visible range of the electromagnetic spectrum. Polymerization of the diacetylenic compounds result in polymerization reaction products that have a color in the visible spectrum less than 570 nm, between 570 nm and 600 nm, or greater than 600 nm depending on their conformation and exposure to external factors. Typically, polymerization of the diacetylenic compounds disclosed herein result in meta-stable blue phase polymer networks that include a polydiacetylene backbone. These meta-stable blue phase polymer networks

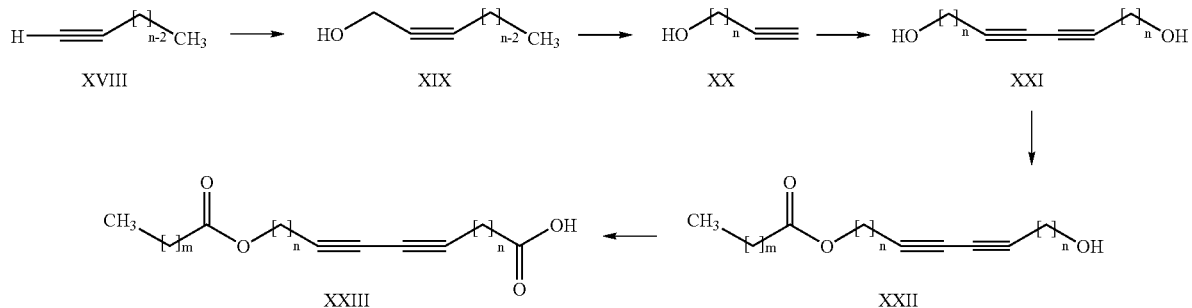

Scheme 1

Compounds of formula XXIII can be prepared via oxidation from compounds of formula XXII by reaction with a suitable oxidizing agent in a suitable solvent such as DMF for example. Suitable oxidizing agents include Jones reagent and pyridinium dichromate for example. The aforesaid reaction is typically run for a period of time from 1 hour to 48 hours, generally 8 hours, at a temperature from 0° C. to 40° C., generally from 0° C. to 25° C.

Compounds of formula XXII can be prepared from compounds of formula XXI by reaction with a suitable acid chloride. Suitable acid chlorides include any acid chloride that affords the desired product such as lauroyl chloride, 1-dodecanoyl chloride, 1-tetradecanoyl chloride, 1-hexadecanoyl chloride, and 1-octadecanoyl chloride for example. Suitable solvents include ether, tetrahydrofuran, dichloromethane, and chloroform, for example. The aforesaid reaction is typically run for a period of time from 1 hour to 24 hours, generally 3 hours, at a temperature from 0° C. to 40° C., generally from 0° C. to 25° C., in the presence of a base such as trialkylamine or pyridine base.

Compounds of formula XXI are either commercially available (e.g. where n is 1-4) or can be prepared from compounds of the formula XVIII via compounds XIX and XX as outlined in Scheme 1 and disclosed in Abrams, Suzanne R.; Shaw, Angela C. "Triple-bond isomerizations: 2- to 9-decyn-1-ol," Org. Synth. (1988), 66, 127-31 and Brandsma, L. "Preparative Acetylenic Chemistry," (Elsevier Pub. Co.: New York, 1971), for example.

Diacetylenic compounds as disclosed herein can also be prepared by reacting compounds of formula XXII with an anhydride such as succinic, glutaric, or phthalic anhydride in the presence of a suitable solvents such as toluene. The aforesaid reaction is typically run for a period of time from undergo a color change from bluish to reddish-orange upon exposure to external factors such as heat, a change in solvent or counterion, if available, or physical stress for example.

Polymerization products of some of the diacetylenic compounds disclosed herein can exhibit a reversible color change and/or a three state color change. For example, after polymerization the resulting blue-phase polymer network can change color to a reddish-orange state upon exposure to heat, a change in solvent or counterion, or physical stress. This reddish-orange polymer network can then change color to a yellowish-orange state upon further exposure to heat, a change in solvent or counterion, or physical stress. Additionally, polymer networks disclosed herein can cycle between these reddish-orange and yellowish-orange states in a reversible manner.

The ability of the diacetylenic compounds and their polymerization products disclosed herein to undergo a visible color change upon exposure to physical stress make them ideal candidates for the preparation of sensing devices for detection of an analyte. The polydiacetylene assemblies formed from the disclosed diacetylene compounds can function as a transducer in biosensing applications.

The structural requirements of a diacetylenic molecule for a given sensing application are typically application specific. Features such as overall chain length, solubility, polarity, crystallinity, and presence of functional groups for further molecular modification all cooperatively determine a diacetylenic molecule's ability to serve as a useful sensing material. For example, in the case of biodetection of an analyte in aqueous media, the structure of the diacetylenic compound should be capable of forming a stable dispersion in water, polymerizing efficiently to a colored material, incorporating appropriate receptor chemistry for binding to an analyte, and transducing that binding interaction by means of a color change. These abilities are dependent on the structural features of the diacetylenic compounds.

The diacetylenic compounds of the present invention possess the capabilities described above and can be easily and efficiently polymerized into polydiacetylene assemblies that undergo the desired color changes. Additionally, the diacetylenic compounds allow for the incorporation of large excesses of unpolymerizable material, such as a receptor described below, while still forming a stable, polymerizable solution.

The disclosed diacetylenic compounds can be synthesized in a rapid high-yielding fashion, including high-throughput methods of synthesis. The presence of functionality in the backbones of the diacetylenic compounds, such as heteroatoms for example, provides for the possibility of easy structural elaboration in order to meet the requirements of a given sensing application. The diacetylenic compounds can be polymerized into the desired polydiacetylene backbone containing network by adding the diacetylene to a suitable solvent, such as water for example, sonicating the mixture, and then irradiating the solution with ultraviolet light, typically at a wavelength of 254 nm. Upon polymerization the solution undergoes a color change to bluish-purple.

Colorimetric Sensors Comprising Polydiacetylene Assemblies

The colorimetric sensors of the present invention comprising the disclosed diacetylene compounds can serve as the basis for the colorimetric detection of a molecular recognition event in solution or coated on a substrate. Such a molecular recognition device can be prepared by adding a receptor to the diacetylene monomer system either prior to or after polymerization. Upon polymerization or thereafter, the receptor is effectively incorporated within the polymer network such that interaction of the receptor with an analyte results in a visible color change due to the perturbation of the conjugated ene-yne polymer backbone.

In one embodiment, the receptor is physically mixed and dispersed among the polydiacetylene assemblies. In an alternative embodiment, the receptor is covalently bonded to the polydiacetylene assemblies. Examples of useful receptors include, but are not limited to surface membrane proteins, enzymes, lectins, antibodies, recombinant proteins, etc.; synthetic proteins; nucleic acids; c-glycosides; carbohydrates; gangliosides; and chelating agents. In one embodiment, the receptor is a phospholipid. In an alternate embodiment, the receptor is a glycerol incorporated into the diacetylene assembly by known methods such as that discussed in Alcaraz, Marie-Lyne; Peng, Ling; Klotz, Phillipe; Goeldner, Maurice, *J. Org. Chem.* 1996, 61, 192-201.

The colorimetric sensors of the present invention formed from the disclosed diacetylene compounds are amenable to a variety of applications that demand cost-effective, stable, accurate, consistent and quick diagnostics outside the laboratory setting. Applications include point-of-care testing, home testing diagnostics, military and industrial detection of air- or water-borne pathogens and VOCs, and food processing.

In one embodiment, the colorimetric sensors can be used for the detection of gram-negative bacteria in biological fluids to diagnose the presence of an infection. For example, the presence of gram-negative bacteria in urine is indicative of a urine infection. A colorimetric sensor comprising the polydiacetylene assemblies of the present invention can indicate the presence of gram-negative bacteria in urine or other biological fluids through color change either in a solution or as a coating on a substrate.

In certain embodiments, the colorimetric sensors of the present invention could be paired with other known diagnostic methods to provide a multi-prong determination of the presence of bacteria or other analytes. For example, in testing urine samples, a colorimetric test detecting leukocyte (white blood cells or WBCs) esterase activity, as described in U.S. Pat. No. 4,299,917 is suggestive of pyuria (pus in the urine) and can be interpreted as an indication of the presence of an infection. A sensor combining a test for leukocytes, in whole or lysed form, as well as a test for gram-negative bacteria based on the polydiacetylene assemblies of the present invention could be used to infer not only the presence of an infection but whether the infection is caused by gram-negative or gram-positive bacteria. A negative result on this combination sensor for gram-negative detection observed on the polydiacetylene portion of the sensor in conjunction with a positive result on the leukocyte portion of the sensor could be interpreted as the presence of a gram-positive bacterial infection. Conversely, a positive result on the gram-negative test would be indicative of a gram-negative bacterial infection. Other potential methods for detecting leukocytes could use fluorometric assays to directly assess the presence of these cells such as described in Khoobehi B. et al. "Fluorescent labeling of blood cells for evaluation of retinal and choroidal circulation," *Ophthaalmic Surg. Lasers* (February 1999), 30(2): 140-5; or to detect peroxide release from activated leukocyctes as disclosed in Mohanty, J. G., Jaffe, Jonathan S., Schulman, Edward S., Raible, Donald G. "A highly sensitive fluorescent micro-assay of H2O2 release from activated human leukocytes using a dihydroxyphenoxazine derivative," *J. Immunological Methods* (1997), 202, 133-141, for example.

Current rapid diagnostic capability, i.e. less than 15 minutes, in urine sample analysis is limited to bacterial detection using the combination of a leukocyte test with a nitrates test, such as the nitrates test described in U.S. Pat. No. 4,434,235 The nitrate test is based on a colorimetric assay capable of detecting nitrates as the by-product of bacteria metabolism. The test is severely limited by its inability to detect the presence of the bacteria directly, and the fact that not all bacteria produce nitrates, and thus some groups of bacteria would not be detected.

For rapid diagnosis of both gram negative and gram positive bacteria, the colorimetric sensor of the present invention and the leukocyte test could be coated on the same substrate to determine the presence or absence of gram negative and gram positive bacteria as describe above. This could minimize the need to wait 16-24 hours for the results of a urine sample culture to identify the class of bacteria before antibiotic treatment begins. In those instances in which an antibiotic is prescribed before the results of the culture are obtained, the antibiotic could be targeted to the class of bacteria based on the sensor test results.

In an alternate embodiment, the colorimetric sensors of the present invention could be used in conjunction with wound dressings to detect the presence of an infection. The sensor could be integrated in the dressing as a layer directly or indirectly in contact with the wound. The sensor could also be inserted into the dressing during use. Alternatively, one could conceive a dressing construction where wound exudate could be directed from the wound to a portion of the dressing not contacting the wound where the sensor is located, through microfluidic channels such as those described in U.S. Pat. No. 6,420,622 B1. The sensor could also be used as a stand-alone diagnostic in the assessment of a wound infection by analyzing the analyte extracted from a wound swab.

A sensor comprising the polydiacetylene assemblies can be obtained without the need to form a film by the conventional LB (Langmuir-Blodgett) process before transferring it onto an appropriate support. Alternatively, the polydiacetylene assemblies can be formed on a substrate using the known LB process as described in A. Ulman, *An Introduction to Ultrathin Organic Films*, Academic Press, New York (1991), pp. 101-219.

The present invention provides biosensing capabilities in a disposable adhesive product. The sensors are self-contained and do not require additional instrumentation to convey a measurable result. Alternatively, use with other analytical instrumentation is possible to further enhance sensitivity, such as fluorescence with the fluorescent "red" phase developed after detection of the analyte. The sensors function to provide a rapid screening device, i.e., less than 30 minutes, and preferably less than 15 minutes, when the detection of a threshold presence of a specific analyte is desired. Additionally, the sensors of the present invention are disposable and relatively inexpensive.

In one embodiment of the invention, the colorimetric sensor comprises a transducer formed from a receptor incorporated within the polydiacetylene assemblies in solution. The solution can be provided in a simple vial system, with the analyte directly added to a vial containing a solution with the transducer specific to the analyte of interest. Alternatively, the colorimetric sensor could comprise multiple vials in a kit, with each vial containing a transducer comprising polydiacetylenes assemblies with incorporated receptors particular to different analytes. For those applications in which the analyte cannot be added directly to the polydiacetylene transducer, a two-part vial system could be used. One compartment of the vial could contain reagents for sample preparation of the analyte physically separated from the second compartment containing the transducer formed from the polydiacetylene assemblies. Once sample preparation is complete, the physical barrier separating the compartments would be removed to allow the analyte to mix with the transducer for detection.

In another embodiment of the present invention, the colorimetric sensor is a rapid indicator in a tape or label format as depicted in FIG. 1. FIG. 1 shows a tape or label 10 coated with a pressure sensitive adhesive 20 and a transducer 30 coated on a substrate 40. Pressure sensitive adhesive 20 can affix tape or label 10 to a surface for direct detection of an analyte. Pressure sensitive adhesive 20 is isolated from transducer 30 containing the polydiacetylene assemblies to potentially minimize adverse effects. In FIG. 1, pressure sensitive adhesive 20 surrounds the transducer 30 located in the center of tape or label 10. In an alternate embodiment (not shown), the pressure sensitive adhesive and the transducer are combined.

Optionally, tape or label 10 will contain a transparent window on the side of tape or label 10 that does not contain pressure sensitive adhesive 20. The window would be centered under transducer 30 to allow the user to view the color change without removing the tape or label 10 from the surface containing the analyte.

Figure 2:
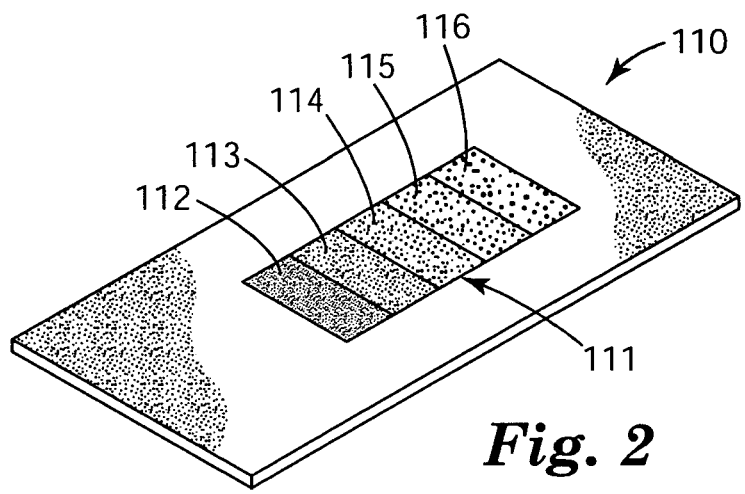
FIG. 2 shows a schematic representation of a colorimetric sensor array of the present invention.

In FIG. 2, the tape or label 110 is shown as array 111 composed of multiple transducers 112, 113, 114, 115, and 116. Each of transducers 112, 113, 114, 115, and 116 could be formed from the same or different polydiacetylene assemblies with each polydiacetylene assembly incorporating the same or different receptor. By varying transducers 112, 113, 114, 115, and 116, array 111 can be designed to detect multiple analytes at various concentration levels. Alternatively, any one of transducers 112, 113, 114, 115 can be replaced with an alternative diagnostic test, such as the leukocyte test.

Figure 3:
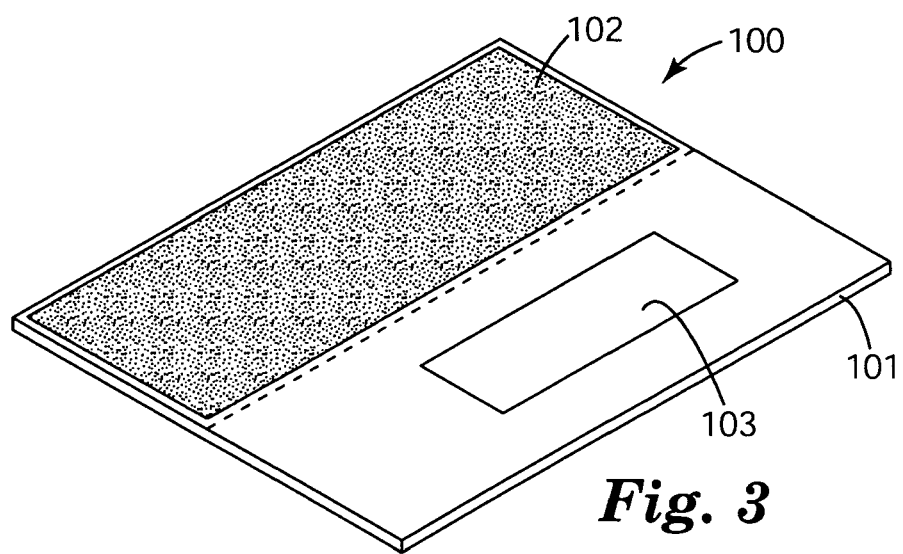
FIG. 3 shows a schematic representation of a colorimetric sensor for contacting the sensor with an analyte.
Figure 4:
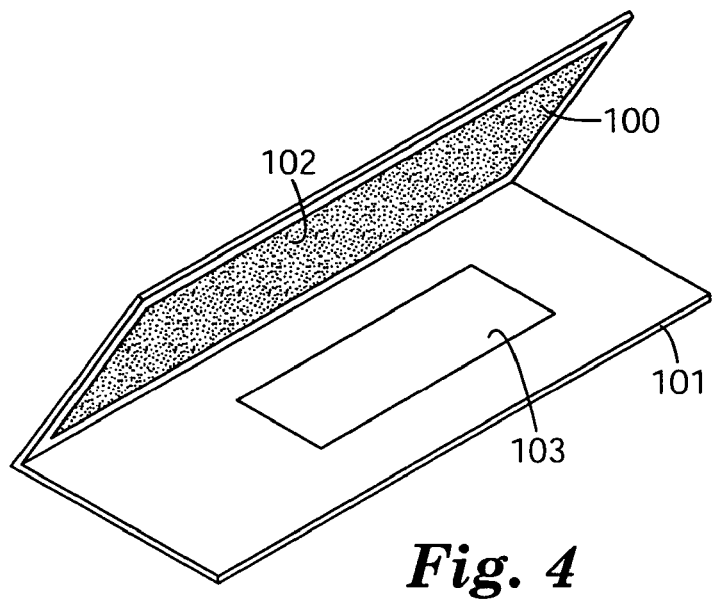
FIG. 4 shows a schematic representation of a foldable colorimetric sensor for contacting the sensor with an analyte.

In another embodiment shown in FIG. 3, tape or label 100 comprises a foldable substrate 101 with pressure sensitive adhesive 102 on one side of foldable substrate 101, and transducer 103 placed on the opposing side of foldable substrate 101 facing pressure sensitive adhesive 102. The surface containing a target analyte could be contacted with pressure sensitive adhesive 102 to collect the sample. Once the sample containing the analyte is collected, the foldable substrate 101 would be folded to contact the pressure sensitive adhesive 102 to transducer 103 as shown in FIG. 4. Optionally, foldable substrate 101 could be perforated to allow separation of foldable substrate 101 into two or more parts, with one part containing pressure sensitive adhesive 102 and another part containing the transducer 103. Both the foldable feature and/or the perforations of foldable substrate 101 allow the user to prevent the transducer from contacting the sample surface that contains the analyte for applications requiring that functionality.

Optionally, foldable substrate 101 in FIG. 3 could also include multiple transducers as shown in FIG. 2 and described above. Further, foldable substrate 101 could include a transparent window on the side opposite transducer 103 for viewing any color change after foldable substrate 101 is folded to contact transducer 103 to pressure sensitive adhesive 102.

Figure 5:
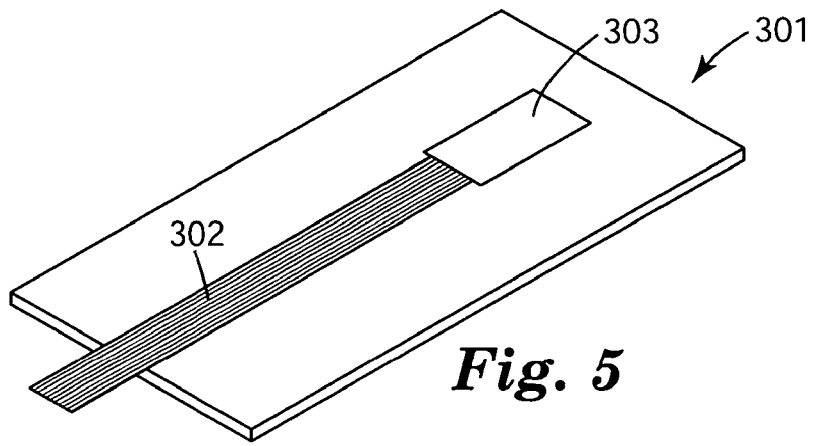
FIG. 5 shows a schematic representation of a colorimetric sensor of the present invention with one type of analyte delivery.
Figure 6:
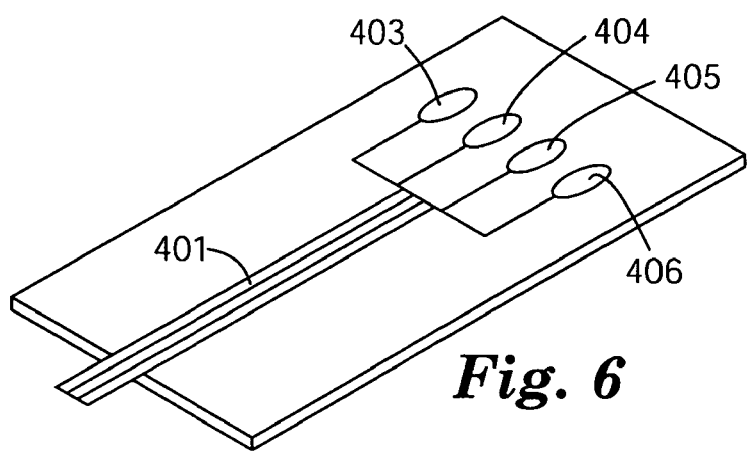
FIG. 6 shows a schematic representation of a colorimetric sensor array of the prevent invention with one type of analyte delivery.

Alternative embodiments are shown in FIGS. 5 and 6 that allow delivery of a fluid sample to the transducer via a microfluidic element such as those described in U.S. Pat. Nos. 6,375,871 and 6,451,191. In FIG. 5, tape or label 301 contains a microfluidic element 302 that delivers the analyte to the transducer 303. In one application, pressure sensitive adhesive could be supplied on tape or label 301 on the side opposite transducer 303 to allow the tape or label to be attached to a surface for storage or holding purposes such as attaching to a wall or container.

In FIG. 6, a microfluidic element 401 is provided on tape or label 402. Microfluidic element 401 delivers the analyte to multiple wells 403, 404, 405, and 406 containing the same or different transducers. Each of the transducers in multiple wells 403, 404, 405, and 406 could be formed from the same or different polydiacetylene assemblies with each polydiacetylene assembly incorporating the same or different receptor. By varying the transducers, multiple wells 403, 404, 405, and 406 can be designed to provide detection for multiple analytes at various concentration levels.

For those applications requiring sample preparation of the analyte, a kit could contain a vial for reagent storage and mixing of the analyte before contacting the colorimetric sensor coated on a two-dimensional substrate. In one embodiment, the kit could comprise a vial for reagent storage and analyte preparation, with a cap system containing the transducer of the present invention coated on a substrate.

The present invention also provides a method for analysis of an analyte, which comprises contacting the abovementioned colorimetric sensor with a solution sample or surface containing an analyte and utilizing an absorption measurement or a visual observation with the naked eye to detect color change in the colorimetric sensor.

In an alternative embodiment, the present invention provides a method for indirect detection of an analyte by selection of a probe with an affinity to bind with both the receptor incorporated into the polydiacetylene assemblies and the analyte. The probe selected will demonstrate a competitive affinity with the analyte. When the analyte of interest is present, the probe will bind to the analyte rather than the receptor on the polydiacetylene backbone, resulting in no color change. If the analyte is absent, the probe will bind to the receptor incorporated on the polydiacetylene backbone, resulting in a color change from blue to red. The probe can contact the transducer after the analyte contacts the transducer, or can be mixed with the analyte prior to the mixture contacting the transducer.

The probe can be contacted with the transducer in solution or coated on a substrate. The probe will be any molecule with an affinity for both the target analyte and the receptor. Possible probes for use in the present invention include membrane disrupting peptides such as alamethicin, magainin, gramicidin, polymyxin B sulfate, and melittin.

Using the indirect method of detection, high sensitivity that provides low levels of detection are possible based on the concentration of probe used. For detection strategy, probe concentrations can be chosen to correspond to desired concentration levels of detection. The method of indirect detection using the probe allows design of the system around the type and concentration of the probe for desired sensitivity in a given application. This allows the transducer to be universal to multiple analytes of interest. For example, a single transducer (polydiacetylene/receptor combination) could serve to detect multiple analytes by varying the probe in contact with the transducer in accordance with the probe's affinity for the analyte.

Substrate Characteristics

The substrates of the present invention can be characterized by contact angle measurements using milli-Q (Millipore) water and methylene iodide (Aldrich) probe liquids. For a contact angle measurement, a goniometer from Rame-Hart is used to measure the contact angle that a drop of a probe liquid forms when placed on a substrate. Although the drop covers a macroscopic area of the substrate, the interaction of the liquid and the surface probes only the outermost 1-5 Ångstroms of the surface. Thus, contact angle analysis provides an accurate and sensitive technique for characterizing surface energetics as discussed in A. Ulman, *An Introduction to Ultrathin Organic Films*, Academic Press, New York (1991), pp. 48-58.

The coating substrates used in the present invention can be considered to encompass two broad categories. The first of these categories include highly flat substrates, such as evaporated gold on atomically flat silicon (111) wafers, atomically flat silicon (111) wafers, or float glass, which are bare and modified with self-assembling monolayers (SAMs) to alter their surface energy in a systematic fashion. The second class of surfaces comprised surfaces with a highly textured topography that included many different classes of materials ranging from paper substrates to polymeric ink receptive coatings to structured polymeric films, microporous films, and membrane materials. Common characteristics amongst these substrates are the large surface roughness and/or porosity. In these highly textured surfaces, the measurements of contact angles and the determination of polar and dispersive surface energies from these contact angle measurements cannot be regarded as an equilibrium characterization of their true thermodynamic energies. For purposes of the present invention, the contact angles indicate an "effective" or "practical" surface energy that can be used to classify these substrates for comparative purposes.

TABLE 1 summarizes the substrates coated with the polydiacetylene assemblies for use as a colorimetric sensor of the present invention. The SAMs used to modify the substrate are listed with the substrate when used. The substrate contact angles as measured with water and methylene iodide are shown, as well as the dispersive and polar components of the surface energy calculated by the Geometric Mean Method as shown in S. Wu; *Polymer Interface and Adhesion*; Marcel Dekker, New York (1982). The last column lists the color of the dry PDA coating.

TABLE 1

| Number | Substrate | Manufacturer | Adv. θ (Water) (°) | Adv. θ (MI) (°) | γ (Dispersive) (dynes/cm) | γ (Polar) (dynes/cm) | Color of Dry Coating |
|---|---|---|---|---|---|---|---|
| 1 | Reverse Chromatography Si Gel Plate | Aldrich; Milwaukee, WI | 158 ± 3.0 | <5 | 101.7 | 39.5 | Blue |
| 2 | Manila Folder Paper | Smead, No. 2-153L-2, Hastings, MN | 115 ± 5.0 | <5 | 76.2 | 7.9 | Blue |
| 3 | Clean Float Glass | Corning Glass Works; Corning, NY | 90 ± 3.8 | 42 ± 2.4 | 39.6 | 0.9 | Blue |
| 4 | Textured Photo Paper | 3M Part No. 34-8506-6373-2; St. Paul, MN | 123 ± 5.4 | <5 | 82.1 | 13.3 | Blue |
| 5 | Gloss Photo Paper | 3M Part No. 34-8506-6378-1; St. Paul, MN | 105 ± 8.0 | 30 ± 1.3 | 58.1 | 1.5 | Blue |
| 6 | PE IR Card | 3M Type 61-100-12; St. Paul, MN | 144 ± 0.6 | <5 | 95.4 | 30.0 | Blue |
| 7 | PTFE IR Card | 3M Type 62; St. Paul, MN | 133 ± 2.3 | 66 ± 2.5 | 44.0 | 7.6 | Blue |
| 8 | Octadecyltrichlorosilane SAM on Si (111) | Gelest, Inc.; Morrisville, PA | 112 ± 1.1 | 69 ± 1.9 | 28.3 | 0.1 | Red |
| 9 | Perfluorodecyl-1H,1H,2H,2H-trichlorosilane | Gelest, Inc.; Morrisville, PA | 113 ± 1.6 | 91 ± 1.3 | 11.7 | 0.7 | Red |

TABLE 1-continued

| Number | Substrate | Manufacturer | Adv. θ (Water) (°) | Adv. θ (MI) (°) | γ (Dispersive) (dynes/cm) | γ (Polar) (dynes/cm) | Color of Dry Coating |
|---|---|---|---|---|---|---|---|
| | on Si (111) Wafer | | | | | | |
| 10 | Octadecyltrichlorosilane SAM on Si (111) | Gelest, Inc.; Morrisville, PA | 112 ± 2.2 | 65 ± 1.8 | 31.9 | 0.3 | Red |
| 11 | Dodecanethiol SAM on Evaporated Au | Aldrich; Milwaukee, WI | 108 ± 3.0 | 65 ± 4.4 | 30.0 | 0 | Red |
| 12 | Octadecanethiol SAM on Evaporated Au | Aldrich; Milwaukee, WI | 107 ± 0.6 | 67 ± 2.7 | 27.7 | 0 | Red |
| 13 | Microstructured PP | 3M sample No. PP-3445; St. Paul, MN | 155 ± 4.5 | 110 ± 6.0 | 9.8 | 2.5 | Red |
| 14 | FC TIPS Membrane | 3M sample; St. Paul, MN | 112 ± 5.5 | 127 ± 11.5 | 0.1 | 8.7 | Red |
| 15 | PVDF Membrane | Millipore Corporation XF1J076T8; Bedford, MA | 86 ± 2.9 | 61 ± 1.1 | 22.8 | 5.4 | Red |
| 16 | Bare Si (111) Wafer | Siltec Corporation; Salem, OR | 52 ± 2.6 | 47 ± 2.8 | 18.7 | 29.2 | Mixed |
| 17 | Bare Evaporated Au | 3M Sample, St. Paul, MN | 97 ± 4.5 | 48 ± 0.6 | 38.9 | 0.1 | Mixed |
| 18 | 11-Mercapto-1-undecanol on Evaporated Au | Aldrich; Milwaukee, WI | 58 ± 1.6 | 38 ± 1.7 | 26.0 | 19.8 | Mixed |
| 19 | 16-Mercaptohexadecanoic on Evaporated Au | Aldrich; Milwaukee, WI | 40 ± 1.6 | 35 ± 6.0 | 21.4 | 35.7 | Mixed |

Figure 7:
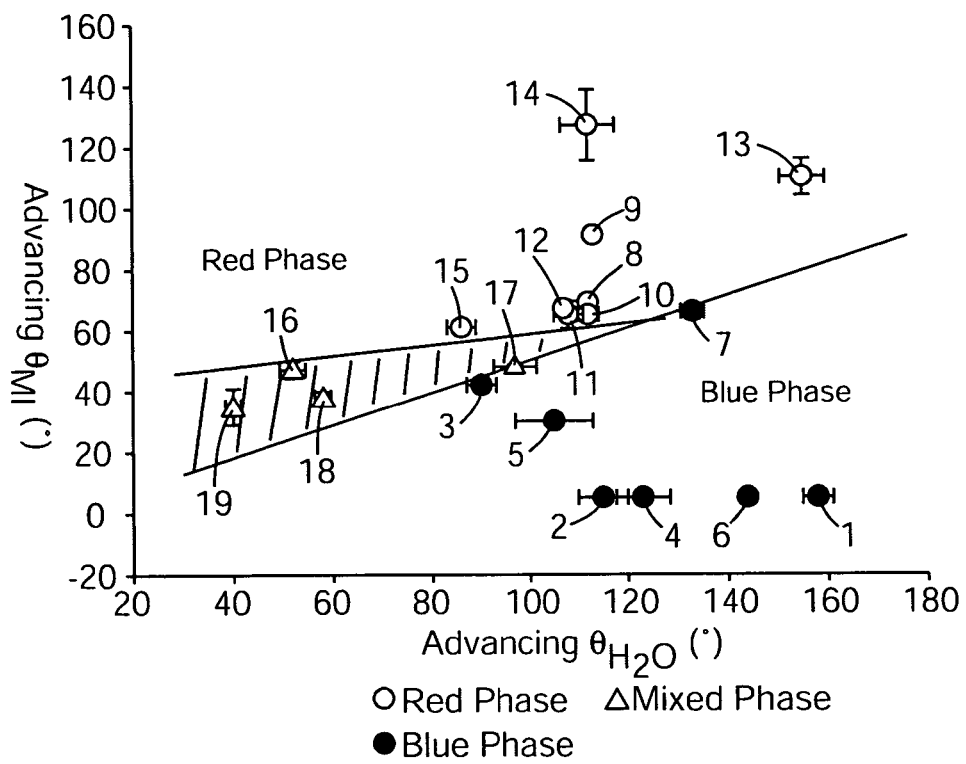
FIG. 7 is a phase diagram showing the colors of the coated and dried polydiacetylene film as a function of the contact angle of the substrate.

FIGS. 6 and 7 show the phase diagram based on the colorimetric observations of the dried coatings and the contact angle analysis of the coated substrates. FIG. 6 shows the resulting color of the coated substrate as a function of advancing contact angle of water versus advancing contact angle of methylene iodide. FIG. 7 shows the resulting color of the coated substrate as a function of the polar component of the substrate surface energy versus the dispersive component of that surface energy as calculated by the Geometric Mean method from the advancing contact angles of water and methylene iodide as provided in S. Wu; *Polymer Interface and Adhesion*; Marcel Dekker, New York (1982). The surfaces for which the polydiacetylene coating remained in its initial blue color are identified by a filled-in circle on each plot. The surfaces identified with a circle are those on which the initial "blue" phase transformed into the red phase upon drying. Finally, the triangular points identify surfaces on which the dry coating showed a mixture of the blue and red phases.

The numbers in TABLE 1 assigned to the various substrates correlate to the symbols in FIGS. 6 and 7.

In one embodiment of the invention that maintains the original "blue" phase of the polydiacetylene assemblies upon drying, the coated substrates exhibit advancing contact angles with methylene iodide below 50° as depicted in FIG. 6. This condition corresponds to substrates characterized by a dispersive component of their surface energy greater than 40 dynes/cm on FIG. 7. For applications requiring the retention of the original "blue" phase, topography and surface energy will impact the effectiveness of the transducer on the substrate in characteristics such as color contrast at detection and shelf-life.

In an alternate embodiment, substrates with these properties that have an advancing contact angle with water less than 90° result in dry coatings containing a mixture of the blue and red phases as depicted in FIG. 6. This condition would correspond to surfaces in which the dispersive surface energy component could be less than 40 dynes/cm but with a polar surface energy component greater than at least 10 dynes/cm in FIG. 7.

EXAMPLES

The present invention should not be considered limited to the particular examples described below, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. All parts, percentages, ratios, etc. in the examples and the rest of the specification are by mole unless indicated otherwise. All solvents and reagents without a named supplier were purchased from Aldrich Chemical; Milwaukee, Wis. Water was purified by the use of a U-V Milli-Q water purifier with a resistivity of 18.2 Mohms/cm.(Millipore, Bedford Mass.)

For those diacetylene mixtures that were probe sonicated, a range of samples were prepared by separating the initial diacetylene solution into several vials for probe sonication over a range of power and times to determine the settings that induce successful self-assembly in the diacetylene monomers. Although probe sonication was done at a power setting of 5 for 1 minute in the following examples, one skilled in the art would know that appropriate adjustments in power and time can empirically create the same result.

Colorimetric response (CR) was determined by the percent change in blue color represented by the equation CR=[(PB$_{initial}$−PB$_{sample}$/PB$_{initial}$]×100 where PB=blue color in sample as determined using Adobe Photoshop, version 5, imaging software.

| Table of Abbreviations | |
| --- | --- |
| Abbreviation or Trade Name | Description |
| 11-Bromo-1-undecanol | Br(CH$_2$)$_{11}$OH |
| 11-Bromoundecanoic acid | Br(CH$_2$)$_{10}$C(O)OH |
| TBDMSCl | Tert-butyldimethylsilyl chloride |
| Diyne-1 | Bis(trimethylsilyl)butadiyne Commercially available from Gelest; Tullytown, PA |
| THF | Tetrahydrofuran |
| 1-Bromododecane | Br(CH$_2$)$_{11}$CH$_3$ |
| TBAF | Tetrabutylammonium fluoride |
| HMPA | Hexamethylphosphoramide |
| 1-Bromohexadecane | Br(CH$_2$)$_{15}$CH$_3$ |
| Methanesulfonyl chloride | |
| CH$_2$Cl$_2$ | Dichloromethane |
| DMF | Dimethylformamide |
| oxalyl chloride | ClCOCOCl |
| DMPC | Dimyristoylphosphatidylcholine; commercially available from Avanti Polar Lipids, Alabaster, Al. |
| ATCC | American Type Culture Collection |
| PDC | Pyridinium dichromate |
| DMAP | 4-(dimethylamino)pyridine |
| KAPA | Potassium 3-aminopropylamide prepared according to Abrams, S. R.; Shaw, A. C. Organic Syntheses, 1988, 66, 127-131. |
| PP | Polypropylene |
| PE | Polyethylene |
| PTFE | Polytetrafluoroethylene |
| PVDF | Polyvinylidenefluoride |

Example 1

Preparation of HO(O)C(CH$_2$)$_3$C≡C—C≡C(CH$_2$)$_4$O(O)C(CH$_2$)$_{10}$CH$_3$

Step 1: Preparation of HO(CH$_2$)$_4$C≡C—C≡C(CH$_2$)$_4$O(O)C(CH$_2$)$_{10}$CH$_3$ In a glass reaction vessel, 600 milligrams of 5,7-dodecadiyn-1,12-diol (HO(CH$_2$)$_4$C≡C—C≡C(CH$_2$)$_4$OH), 0.275 milliliters of pyridine and 10 milliliters of THF were mixed. To this solution was added 676 milligrams of lauroyl chloride and the resulting mixture was stirred for 15 hours. The mixture was then diluted with diethyl ether and washed with 0.1 N HCl and brine. The organic layer was separated, dried over MgSO$_4$, filtered and the solvent was removed to yield a white solid. The solid was purified over silica gel (gradient from 25% to 50% by volume ethyl acetate in hexanes) to yield 570 milligrams of HO(CH$_2$)$_4$C≡C—C≡C(CH$_2$)$_4$O(O)C(CH$_2$)$_{10}$CH$_3$ as a white solid.

Step 2: Preparation of HO(O)C(CH$_2$)$_3$C≡C—C≡C(CH$_2$)$_4$O(O)C(CH$_2$)$_{10}$CH$_3$ In a glass reaction vessel, 377 milligrams of HO(CH$_2$)$_4$C≡C—C≡C(CH$_2$)$_4$O(O)C(CH$_2$)$_{10}$CH$_3$ prepared in Step 1 was dissolved in 3 milliliters of DMF and 1.32 grams of PDC was added. The resulting mixture was stirred for 8 hours, and then worked up with water and diethyl ether. The combined ether layers were dried over MgSO$_4$, filtered and the solvent was removed to yield a white solid. The solid was purified over silica gel eluting with 25/74/1 of ethyl acetate/hexanes/formic acid by volume to yield 0.21 grams of HO(O)C(CH$_2$)$_3$C≡C—C≡C(CH$_2$)$_4$O(O)C(CH$_2$)$_{10}$CH$_3$ as a white solid.

Examples 2-5

Preparation of HO(O)C(CH$_2$)$_{a-1}$C≡C—C≡C(CH$_2$)$_a$O(O)C(CH$_2$)$_b$CH$_3$

The same procedure described in Example 1 was followed using the diol and acid chloride in Step 1 shown in Table 2 to give the compounds with the general structure HO(O)C(CH$_2$)$_{a-1}$C≡C—C≡C(CH$_2$)$_a$O(O)C(CH$_2$)$_b$CH$_3$ (a and b are defined in Table 2).

TABLE 2

| Example | Diol, a value | Acid Chloride, b value |
| --- | --- | --- |
| 2 | HO(CH$_2$)$_3$C≡C—C≡C(CH$_2$)$_3$OH, a = 3 | CH$_3$(CH$_2$)$_{14}$C(O)Cl, b = 14 |
| 3 | HO(CH$_2$)$_4$C≡C—C≡C(CH$_2$)$_4$OH, a = 4 | CH$_3$(CH$_2$)$_{12}$C(O)Cl, b = 12 |
| 4 | HO(CH$_2$)$_4$C≡C—C≡C(CH$_2$)$_4$OH, a = 4 | CH$_3$(CH$_2$)$_{14}$C(O)Cl, b = 14 |
| 5 | HO(CH$_2$)$_4$C≡C—C≡C(CH$_2$)$_4$OH, a = 4 | CH$_3$(CH$_2$)$_{16}$C(O)Cl, b = 16 |

Example 6

Preparation of HO(O)C(CH$_2$)$_2$C(O)O(CH$_2$)$_4$C≡C—C≡C(CH$_2$)$_4$O(O)C(CH$_2$)$_{12}$CH$_3$ Step 1: Preparation of HO(CH$_2$)$_4$C≡C—C≡C(CH$_2$)$_4$O(O)C(CH$_2$)$_{12}$CH$_3$ In a glass reaction vessel, 4.99 grams of 5,7-dodecadiyn-1,12-diol (HO(CH$_2$)$_4$C≡C—C≡C(CH$_2$)$_4$OH), 2.2. grams of pyridine and 50 milliliters of THF were mixed. To this solution was added 6.34 grams of myristol chloride and the resulting mixture was stirred for 15 hours. The mixture was then diluted with diethyl ether and washed with 0.1 N HCl and brine. The organic layer was separated, dried over MgSO$_4$, filtered and the solvent was removed to yield a white solid. The solid was purified over silica gel (15% by volume of ethyl acetate in dichloromethane to 100% theyl acetate gradient) to yield 5.0 grams of HO(CH$_2$)$_4$C≡C—C≡C(CH$_2$)$_4$O(O)C(CH$_2$)$_{12}$CH$_3$ as a white solid.

Step 2: Preparation of HO(O)C(CH$_2$)$_2$C(O)O(CH$_2$)$_4$C≡C—C≡C(CH$_2$)$_4$O(O)C(CH$_2$)$_{12}$CH$_3$ In a sealable tube, 1.41 grams of HO(CH$_2$)$_3$C≡C—C≡C(CH$_2$)$_4$O(O)C(CH$_2$)$_{12}$CH$_3$ prepared in Step 1, 0.435 grams of succinic anhydride, 13 milliliters of toluene and 0.106 grams of DMAP were combined and the tube was sealed. The mixture was heated to 105° C. for 14.5 hours, the reaction was cooled to room temperature, 0.15 milliliters of water was added, the tube was resealed and again heated to 105° C. for 30 minutes. The mixture was then diluted with diethyl ether and washed with 0.1 N HCl and brine. The organic layer was separated, dried over MgSO$_4$, filtered and the solvent was removed to yield a white solid. The solid was purified over silica gel eluting with 10/89/1 of ethyl acetate/dichloromethane/formic acid by volume to yield 1.70 grams of HO(O)C(CH$_2$)$_2$C(O)O(CH$_2$)$_4$C≡C—C≡C(CH$_2$)$_4$O(O)C(CH$_2$)$_{12}$CH$_3$ as a white solid.

Examples 7-17

Preperation of $HO(O)C(CH_2)_2C(O)O(CH_2)_a$
$C{\equiv}C{-}C{\equiv}C(CH_2)_aO(O)C(CH_2)_bCH_3$ The same procedure described in Example 6 was followed using the diol and acid chloride in Step 1 shown in Table 3 to give the compounds with the general structure $HO(O)C(CH_2)_2C(O)O(CH_2)_aC{\equiv}C{-}C{\equiv}C(CH_2)_aO(O)C(CH_2)_bCH_3$ (a and b are defined in Table 3).

TABLE 3

| Example | Diol, a value | Acid Chloride, b value |
|---|---|---|
| 7 | $HO(CH_2)_2C{\equiv}C{-}C{\equiv}C(CH_2)_2OH$, a = 2 | $CH_3(CH_2)_{10}C(O)Cl$, b = 10 |
| 8 | $HO(CH_2)_2C{\equiv}C{-}C{\equiv}C(CH_2)_2OH$, a = 2 | $CH_3(CH_2)_{12}C(O)Cl$, b = 12 |
| 9 | $HO(CH_2)_2C{\equiv}C{-}C{\equiv}C(CH_2)_2OH$, a = 2 | $CH_3(CH_2)_{14}C(O)Cl$, b = 14 |
| 10 | $HO(CH_2)_2C{\equiv}C{-}C{\equiv}C(CH_2)_2OH$, a = 2 | $CH_3(CH_2)_{16}C(O)Cl$, b = 16 |
| 11 | $HO(CH_2)_3C{\equiv}C{-}C{\equiv}C(CH_2)_3OH$, a = 3 | $CH_3(CH_2)_{10}C(O)Cl$, b = 10 |
| 12 | $HO(CH_2)_3C{\equiv}C{-}C{\equiv}C(CH_2)_3OH$, a = 3 | $CH_3(CH_2)_{12}C(O)Cl$, b = 12 |
| 13 | $HO(CH_2)_3C{\equiv}C{-}C{\equiv}C(CH_2)_3OH$, a = 3 | $CH_3(CH_2)_{14}C(O)Cl$, b = 14 |
| 14 | $HO(CH_2)_3C{\equiv}C{-}C{\equiv}C(CH_2)_3OH$, a = 3 | $CH_3(CH_2)_{16}C(O)Cl$, b = 16 |
| 15 | $HO(CH_2)_4C{\equiv}C{-}C{\equiv}C(CH_2)_4OH$, a = 4 | $CH_3(CH_2)_{10}C(O)Cl$, b = 10 |
| 16 | $HO(CH_2)_4C{\equiv}C{-}C{\equiv}C(CH_2)_4OH$, a = 4 | $CH_3(CH_2)_{14}C(O)Cl$, b = 14 |
| 17 | $HO(CH_2)_4C{\equiv}C{-}C{\equiv}C(CH_2)_4OH$, a = 4 | $CH_3(CH_2)_{16}C(O)Cl$, b = 16 |

Example 18

Preparation of $HO(O)C(CH_2)_2C(O)O(CH_2)_5$
$C{\equiv}C{-}C{\equiv}C(CH_2)_5O(O)C(CH_2)_{10}CH_3$

Step 1: Preparation of $HO(CH_2)_5C{\equiv}C{-}C{\equiv}C(CH_2)_5OH$ $HO(CH_2)_5C{\equiv}CH$ was prepared by the KAPA-promoted isomerization of $HOCH_2C{\equiv}C(CH_2)_3CH_3$ prepared according to Millar, J. G.; Oehlschlager, A. C. J. Org. Chem. 1984, 49, 2332-2338 or $HO(CH_2)_2C{\equiv}C(CH_2)_2CH_3$ (commercially available from GFS Chemicals; Powell, Ohio). Oxidative coupling of $HO(CH_2)_5C{\equiv}CH$ was carried out in a glass reaction vessel by dissolving 6.95 grams $HO(CH_2)_5C{\equiv}CH$ in pyridine/methanol (2.0 mL/6.2 mL) and adding 307 grams of CuCl followed by stirring in the presence of oxygen until all the starting material was consumed. The reaction mixture was worked up with diethyl ether and 4N HCl, the combined organic layers were dried over $MgSO_4$, filtered and concentrated. Recrystallization of the residue from 1/1 hexanes/tert-butyl methyl ether yielded 5.35 grams of $HO(CH_2)_5C{\equiv}C{-}C{\equiv}C(CH_2)_5OH$.

Step 2: Preparation of $HO(CH_2)_5C{\equiv}C{-}C{\equiv}C(CH_2)_5O(O)C(CH_2)_{10}CH_3$ The same procedure described in Example 6 Step 1 was followed except that instead of 5,7-dodecadiyn-1,12-diol the diol prepared in Step 1 above was used.

Step 3: Preparation of $HO(O)C(CH_2)_2C(O)O(CH_2)_5$
$C{\equiv}C{-}C{\equiv}C(CH_2)_5O(O)C(CH_2)_{10}CH_3$ The same procedure described in Example 6 Step 2 was followed.

Examples 19-21

Preparation of $HO(O)C(CH_2)_2C(O)O(CH_2)_5$
$C{\equiv}C{-}C{\equiv}C(CH_2)_5O(O)C(CH_2)_bCH_3$ The same procedure described in Example 18 was followed using the diol and acid chloride in Step 2 shown in Table 4 to give the compounds with the general structure $HO(O)C(CH_2)_2C(O)O(CH_2)_5C{\equiv}C{-}C{\equiv}C(CH_2)_5O(O)C(CH_2)_bCH_3$ (b is defined in Table 4).

TABLE 4

| Example | Diol | Acid Chloride, b value |
|---|---|---|
| 19 | $HO(CH_2)_5C{\equiv}C{-}C{\equiv}C(CH_2)_5OH$ | $CH_3(CH_2)_{12}C(O)Cl$, b = 12 |
| 20 | $HO(CH_2)_5C{\equiv}C{-}C{\equiv}C(CH_2)_5OH$ | $CH_3(CH_2)_{14}C(O)Cl$, b = 14 |
| 21 | $HO(CH_2)_5C{\equiv}C{-}C{\equiv}C(CH_2)_5OH$ | $CH_3(CH_2)_{16}C(O)Cl$, b = 16 |

Examples 22-25

Preparation of $HO(O)C(CH_2)_2C(O)O(CH_2)_6$
$C{\equiv}C{-}C{\equiv}C(CH_2)_6O(O)C(CH_2)_bCH_3$ The same procedure described in Example 18 Step 1 was followed to prepare the diol $HO(CH_2)_6C{\equiv}C{-}C{\equiv}C(CH_2)_6OH$ starting from 1-heptyne. The remaining procedure for Example 18 was followed using the diol and acid chloride in Step 2 shown in Table 5 to give the compounds with the general structure $HO(O)C(CH_2)_2C(O)O(CH_2)_6C{\equiv}C{-}C{\equiv}C(CH_2)_6O(O)C(CH_2)_bCH_3$ (b is defined in Table 5)

TABLE 5

| Example | Diol | Acid Chloride, b value |
|---|---|---|
| 22 | $HO(CH_2)_6C{\equiv}C{-}C{\equiv}C(CH_2)_6OH$ | $CH_3(CH_2)_{10}C(O)Cl$, b = 10 |
| 23 | $HO(CH_2)_6C{\equiv}C{-}C{\equiv}C(CH_2)_6OH$ | $CH_3(CH_2)_{12}C(O)Cl$, b = 12 |
| 24 | $HO(CH_2)_6C{\equiv}C{-}C{\equiv}C(CH_2)_6OH$ | $CH_3(CH_2)_{14}C(O)Cl$, b = 14 |
| 25 | $HO(CH_2)_6C{\equiv}C{-}C{\equiv}C(CH_2)_6OH$ | $CH_3(CH_2)_{16}C(O)Cl$, b = 16 |

Examples 26-29

Preparation of $HO(O)C(CH_2)_2C(O)O(CH_2)_7$
$C{\equiv}C{-}C{\equiv}C(CH_2)_7O(O)C(CH_2)_bCH_3$ The same procedure described in Example 18 Step 1 was followed to prepare the diol $HO(CH_2)_7C{\equiv}C{-}C{\equiv}C(CH_2)_7OH$ staring from 1-octyne. The remaining procedure for Example 18 was followed using the diol and acid chloride in Step 2 shown in Table 6 to give the compounds with the general structure $HO(O)C(CH_2)_2C(O)O(CH_2)_7C{\equiv}C{-}C{\equiv}C(CH_2)_7O(O)C(CH_2)_bCH_3$ (b is defined in Table 6).

TABLE 6

| Example | Diol | Acid Chloride |
|---|---|---|
| 26 | $HO(CH_2)_7C{\equiv}C{-}C{\equiv}C(CH_2)_7OH$ | $CH_3(CH_2)_{10}C(O)Cl$, b = 10 |
| 27 | $HO(CH_2)_7C{\equiv}C{-}C{\equiv}C(CH_2)_7OH$ | $CH_3(CH_2)_{12}C(O)Cl$, b = 12 |
| 28 | $HO(CH_2)_7C{\equiv}C{-}C{\equiv}C(CH_2)_7OH$ | $CH_3(CH_2)_{16}C(O)Cl$, b = 16 |

Examples 29-32

Preparation of $HO(O)C(CH_2)_2C(O)O(CH_2)_9$ $C\equiv C-C\equiv C(CH_2)_9O(O)C(CH_2)_bCH_3$ The same procedure described in Example 18 Step 1 was followed to prepare the diol $HO(CH_2)_9C\equiv C-C\equiv C(CH_2)_9OH$ staring from 1-decyne. The remaining procedure for Example 18 was followed using the diol and acid chloride in Step 2 shown in Table 7 to give the compounds with the general structure $HO(O)C(CH_2)_2C(O)O(CH_2)_9C\equiv C-C\equiv C(CH_2)_9O(O)C(CH_2)_bCH_3$ (b is defined in Table 7).

TABLE 7

| Example | Diol | Acid Chloride, b value |
|---|---|---|
| 29 | $HO(CH_2)_9C\equiv C-C\equiv C(CH_2)_9OH$ | $CH_3(CH_2)_{10}C(O)Cl$, b = 10 |
| 30 | $HO(CH_2)_9C\equiv C-C\equiv C(CH_2)_9OH$ | $CH_3(CH_2)_{12}C(O)Cl$, b = 12 |
| 31 | $HO(CH_2)_9C\equiv C-C\equiv C(CH_2)_9OH$ | $CH_3(CH_2)_{14}C(O)Cl$, b = 14 |
| 32 | $HO(CH_2)_9C\equiv C-C\equiv C(CH_2)_9OH$ | $CH_3(CH_2)_{16}C(O)Cl$, b = 16 |

Example 33

Preparation of $HO(O)C(CH_2)_3C(O)O(CH_2)_4$ $C\equiv C-C\equiv C(CH_2)_4O(O)C(CH_2)_{12}CH_3$ The same procedure described in Example 6 was followed except that in Step 2 glutaric anhydride was used in place of succinic anhydride.

Example 34

Preparation of $HO(O)CHC=CHC(O)O(CH_2)_4$ $C\equiv C-C\equiv C(CH_2)_4O(O)C(CH_2)_{14}CH_3$ The same procedure described in Example 6 was followed except that in Step 1 $CH_3(CH_2)_{14}C(O)Cl$ was used instead of $CH_3(CH_2)_{12}C(O)Cl$ and in Step 2 maleic anhydride was used in place of succinic anhydride.

Example 35

Preparation of $HO(O)C(1,2-C_6H_4)C(O)O(CH_2)_4$ $C\equiv C-C\equiv C(CH_2)_4O(O)C(CH_2)_{12}CH_3$ The same procedure described in Example 6 was followed except that in Step 2 phthalic anhydride was used in place of succinic anhydride.

Example 36

Preparation of $HO(O)C(CH_2)_2C(O)O(CH_2)_4$ $C\equiv C-C\equiv C(CH_2)_4O(CH_2)_{11}CH_3$ Step 1: Preparation of $HO(CH_2)_4C\equiv C-C\equiv C(CH_2)_4O(CH_2)_{11}CH_3$ In a glass reaction vessel, a suspension of 120 milligrams of sodium hydride was prepared in 10 mL dry DMF and 972 milligrams of 5,7-dodecadiyn-1,12-diol ($HO(CH_2)_4C\equiv C-C\equiv C(CH_2)_4OH$), was added. After stirring for 5 minutes, 1.31 grams of $CH_3(CH_2)_{11}Br$ was added and the resulting mixture was stirred for 15 hours. The mixture was then quenched by addition of saturated $NH_4Cl$ solution and diluted with 100 milliliters of diethyl ether. The organic layer was separated and washed 3 times with brine, dried over $MgSO_4$, filtered and the solvent was removed to yield a yellow oil. The oil was purified over silica gel (25%-35% by volume of ethyl acetate in hexane gradient) to yield 606 milligrams of $HO(CH_2)_4C\equiv C-C\equiv C(CH_2)_4O(CH_2)_{11}CH_3$ as a white solid.

Step 2: Preparation of $HO(O)C(CH_2)_2C(O)O(CH_2)_4$ $C\equiv C-C\equiv C(CH_2)_4O(CH_2)_{11}CH_3$ In a sealable tube, 181 milligrams of $HO(CH_2)_4C\equiv C-C\equiv C(CH_2)_4O(CH_2)_{11}CH_3$ prepared in Step 1, 63 milligrams of succinic anhydride, 2 milliliters of toluene and 15 milligrams of DMAP were combined and the tube was sealed. The mixture was heated to 110° C. for 16 hours, the reaction was cooled to room temperature, 3 drops of water were added, the tube was resealed and again heated to 110° C. for 30 minutes. The mixture was then diluted with diethyl ether and washed with 0.1 N HCl and brine. The organic layer was separated, dried over $MgSO_4$, filtered and the solvent was removed to yield a white solid. The solid was purified over silica gel eluting with 10/89/1 of ethyl acetate/dichloromethane/formic acid by volume to yield $HO(O)C(CH_2)_2C(O)O(CH_2)_4C\equiv C-C\equiv C(CH_2)_4O(CH_2)_{11}CH_3$ as a white solid.

Examples 37-41

Preparation of $HO(O)C(CH_2)_2C(O)O(CH_2)_a$ $C\equiv C-C\equiv C(CH_2)_aO(CH_2)_bCH_3$ The same procedure described in Example 37 was followed using the diol and alkyl bromide in Step 1 shown in Table 8 to give the compounds with the general structure $HO(O)C(CH_2)_2C(O)O(CH_2)_aC\equiv C-C\equiv C(CH_2)_aO(CH_2)_bCH_3$ (a and b are defined in Table 8).

TABLE 8

| Example | Diol, a value | Alkyl Bromide, b value |
|---|---|---|
| 37 | $HO(CH_2)_2C\equiv C-C\equiv C(CH_2)_2OH$, a = 4 | $CH_3(CH_2)_bBr$, b = 13 |
| 38 | $HO(CH_2)_2C\equiv C-C\equiv C(CH_2)_2OH$, a = 4 | $CH_3(CH_2)_bBr$, b = 15 |
| 39 | $HO(CH_2)_2C\equiv C-C\equiv C(CH_2)_2OH$, a = 4 | $CH_3(CH_2)_bBr$, b = 17 |
| 40 | $HO(CH_2)_2C\equiv C-C\equiv C(CH_2)_2OH$, a = 5 | $CH_3(CH_2)_bBr$, b = 11 |
| 41 | $HO(CH_2)_3C\equiv C-C\equiv C(CH_2)_3OH$, a = 5 | $CH_3(CH_2)_bBr$, b = 13 |

Example 42

A sample of 10.1 milligrams of the compound prepared in Example 6 was placed in a glass vessel and suspended in 5 milliliters of isopropanol. The mixture was heated to boiling and 10 milliliters of 70° C. water was added. The resulting solution was boiled until the temperature reached 95° C. indicating the nearly all of the isopropanol had boiled off. The solution was cooled to room temperature and then to 4° C. for 16 hours. A 2 milliliter aliquot of the solution was exposed 254 nanometer light for 10 minutes, producing a dark blue color indicative that polymerization had occurred.

Example 43

Detection of a Membrane Peptide in Solution

A sample of 1.0 milliMolar concentration of diacetylene monomer prepared as in Example 6 and DMPC (6:4) in Tris buffer (2 mM, pH=8.5) was prepared in a glass vessel, bath sonicated in a Bronson Model #1510 bath sonicator (commercially available from VWR Scientific Products; West Chester, Pa.) for 30 minutes, and placed in a 4° C. refrigerator for about 16 hours. The sample was then filtered through a 1.2 μm syringe filter, and polymerized by irradiating the sample beneath a 254 nm UV lamp (commercially available from VWR Scientific Products; West Chester, Pa.) at a distance of 3 cm for 10 minutes. Polymerization results in the observation of a distinct, bluish-purple color.

The detection property of the solution was determined by the addition of ~80 μL of a polymyxin B sulfate solution (10,050 units/mL) to the sample. This resulted in a rapid colorimetric response that could easily be determined visually as a change from blue to red and quantified by UV-vis spectroscopy as a shift from peak absorbance at 640 nm to a peak absorbance at 540 nm in spectra taken after one hour at room temperature.

Example 44

Detection of a Membrane Peptide on a Substrate

The polymerized PDA/DMPC mixture prepared in Example 43 was coated onto a piece of a reverse-phase C-18 silica gel plate. The solution was spotted on the plate and allowed to dry at room temperature resulting in blue spots on the test plate. To test this solid state form of the sensor, a test solution (40 μL) of a polymyxin B sulfate (10,050 units/mL) was added to the sample spot. This resulted in an immediate (<15 seconds) color change from blue to pink. A control test using only milli-Q water (50 μL) showed no color change.

Example 45

Detection of Peptide-Membrane Interactions in Solution

A mixture of diacetylene monomer from Example 6 and DMPC (6:4) was weighed into a vial and suspended in Tris buffer (2 mM, pH=8.5) to produce a 1 mM concentration solution and a polymerized detection solution was prepared as in Example 43.

The detection property of the solution was determined by the addition of ~50 μL of a 1 mM mellitin solution to the sample. This resulted in a rapid colorimetric response that could easily be determined visually as a change from blue to red and quantified by UV-vis spectroscopy as a shift from peak absorbance at 640 nm to a peak absorbance at 540 nm in spectra taken after one hour at room temperature.

Example 46

Detection of Peptide-Membrane Interactions on a Substrate

A test plate was made using the polymerized detector solution of Example 45 using the same procedure as in Example 44. Several spots (40 μl each) of the polymerized solutions were placed onto a piece of a reverse-phase C-18 silica gel plate. The solutions were allowed to dry at room temperature resulting in blue spots. To test the substrates' ability to detect peptides, two samples containing 15 and 30 nanomoles of mellitin respectively were added to the different spots on the test plate. This resulted in an immediate (<15 seconds) color change from blue to red. Control samples of milli-Q water spotted on separate test spots showed no color change.

Example 47

Detection of Interfacial Enzymatic Catalysis by Phospholipase A2 in Solution A detection solution was prepared as in Example 45. The detection properties of the solutions were determined by the addition of ~50 μL of a 75 μM Phospholipase A2 solution to each of the samples. This resulted in a colorimetric response that could easily be determined visually as a change from blue to red and quantified by UV-vis spectroscopy as a shift from peak absorbance at 640 nm to a peak absorbance at 540 nm in spectra taken after one hour at room temperature.

Example 48

Attempted Detection of Peptide-Membrane Interactions using Commercially Available Diacetylenic Monomers on a Substrate Mixtures of commercially available 10,12-tricosadiynoic acid (available from GFS Chemicals; Powell, Ohio) and DMPC (6:4) were used to create a detector solution and test plate as in Example 44. The polymerization resulted in the observation of a distinct, bluish-purple color. On spotting the detector solution on the test plates some of the solutions dried resulting in a color change to a red spot while other samples dried to a blue colored spot.

To test the peptide-membrane interaction detection properties of the polymerized assemblies on a substrate, 30 nanomoles of mellitin (commercially available from Sigma Aldrich; St. Louis, Mo.) was added to the spots that dried to a blue color. This resulted in either no color change or a splotchy appearance that reflected a CR less than 5% depending on the preparation of the solution.

Example 49

Attempted Detection of Peptide-Membrane Interactions using Commercially Available Diacetylenic Monomers on a 2-D Substrate Example 48 was repeated, except that to test the peptide-membrane interaction detection properties of the polymerized assemblies on the substrate, 50 μL of a polymyxin B sulfate solution (10,050 units/mL) was added to each of the spots on the test plate. This resulted in a splotchy appearance that reflected a CR less than 5% of color change depending on the preparation of the solution.

Example 50

Indirect Detection of E. coli on a Substrate

Test plates were made as in Example 46.

To test the detection of E. coli, a polymyxin B sulfate solution (10,050 units/mL) was added to a vial containing only milli-Q water and to a vial containing a suspension of E. coli [ATCC25922, ~$10^9$ bacteria/mL in milli-Q water].

After allowing the two samples to sit for 30 minutes, they were filtered through a 0.45 μm syringe filter and 40 μL of each of the eluents was placed onto dried spots of the sensor mixture. After 15 minutes the liquid was removed and the plates were examined. The sample with no *E. coli* and only polymyxin B showed a color change to red while those samples with both *E. coli* and polymyxin B show no dramatic color change.

Example 51

Detection of *E. coli* in a Biological Fluid on a Substrate

A mixture of diacetylene monomer as prepared in Example 6 and DMPC (6:4) was weighed into a vial and suspended in HEPES buffer (5 mM, pH=7.2) to produce a 1 mM solution. The solution was then probe sonicated using a Model XL2020 probe sonicator (commercially available from Misonix, Inc.; Farmington, N.Y.) for 1 minute at a power setting of 5, and placed into a 4° C. refrigerator overnight (~16 hours). The sample was filtered through a 1.2 μm syringe filter and polymerization of a stirring solution was achieved by irradiating the sample beneath a 254 nm UV lamp at a distance of 3 cm for 20 minutes, resulting in the observation of a blue color. Using a syringe, several spots (40 μl each) of the polymerized solution were placed onto a piece of a reverse-phase C-18 silica gel plate. The spots were allowed to dry at room temperature resulting in blue spots. To test the detection of *E. coli*, a polymyxin B sulfate solution (10,050 units/mL) was added to a solution of human urine and a solution of human urine contaminated with *E. coli* [ATCC25922, ~$10^9$ bacteria/mL in milli-Q water]. After allowing the samples to incubate for 30 minutes at 37° C., the samples were cooled to room temperature and 40 μL of each eluent was placed onto a dried spot of the PDA/DMPC solution. After 40 minutes the liquid was removed and the plates were examined. The spots showed a substantial color change for the sample with no *E. coli*. and only polymyxin B present while the sample with *E. coli* and polymyxin B present exhibited little change in color.

Example 52

Detection of Lipopolysaccharide on a Substrate

Mixtures of diacetylene monomer as prepared in Example 6 and DMPC (6:4) were weighed into vials and suspended in HEPES buffer (5 mM, pH=7.2) to produce a 1 mM solution. Test plates on a reverse-phase C-18 silica gel plate were then prepared as in Example 43. To test the detection of lipopolysaccharide, 1000 μL of a polymyxin B sulfate solution (628 units/mL) was added to a 1 mL solution of endotoxin free water and a 1 mL solution of endotoxin free water contaminated with lipopolysaccharide (10,000 units/mL). After allowing the samples to incubate for 30 minutes at 37° C., the samples were cooled to room temperature and 40 μL of each solution was placed onto a dried spot of the PDA/DMPC solution. After 60 minutes the liquid was removed and the plates were examined. The sample with no lipopolysaccharide showed a color change to red while the solution with lipopolysaccharide and polymyxin B showed no color change.

Example 53

Detection of Lipopolysaccharide on a 2-D Substrate Using Glycerol

Mixtures of diacetylene monomer as prepared in Example 6 and tetradecanoic acid 12-(4,4,-dihydroxy-butylroxy)-dodeca-5,7-diynyl ester (1:1) were weighed into vials and suspended in HEPES buffer (5 mM, pH=7.2) to produce a 1 mM solution. The solutions were then probe sonicated using a Model XL2020 probe sonicator (commercially available from Misonix, Inc.; Farmington, N.Y.) for 1 minute at a power setting of 5, and then placed into a 4° C. refrigerator overnight (~16 hours). The samples were filtered through a 1.2 μm syringe filter and polymerization of a stirring solution was achieved by irradiating the sample beneath a 254 nm UV lamp at a distance of 3 cm for 60 seconds, resulting in the observation of an intense blue color. Using a syringe, several spots (40 μl each) of the polymerized solutions were placed onto a piece of a reverse-phase C-18 silica gel plate. The solutions were allowed to dry at room temperature resulting in blue spots. To test the detection of lipopolysaccharide, a polymyxin B sulfate solution (5025 units/mL) was added to a solution of endotoxin free water and a solution of endotoxin free water contaminated with lipopolysaccharide. After allowing the samples to incubate for 30 minutes at 37° C., the samples were cooled to room temperature and 500 μL of each solution was placed onto a dried spot of the PDA/DMPC solution. After 15 minutes of gentle shaking, the liquid was removed and the plates were examined. This resulted in a colorimetric response that could easily be determined visually as a change from blue to red in the absence of lipopolysaccharide.

Example 54

Characterization of Substrates Amenable to Maintain the Active Phase of the Polydiacetylene Assemblies To determine the substrate characteristics identified in Table 1, surfaces were prepared in the following manner for evaluation. The gold surfaces were prepared by evaporation of gold onto a chromium primed polished silicon wafer. The resulting surface was highly reflective with an rms surface roughness less than 15 Ångstroms as measured by Atomic Force Microscopy (AFM) using Nanoscope Command Reference Manual Version 4.42; Digital Instruments; Sections 12.5 and 12.6. The gold surfaces were dusted prior to use using a dry nitrogen stream.

The glass surfaces were prepared by cleaning in an oxidizing bath (commercially available from Nochromix) overnight, followed by copious rinsing in milli-Q water until the rinse water could maintain a uniform sheet over the glass surface without de-wetting. The glass surfaces were dusted prior to use using a dry nitrogen stream.

Silicon wafer surfaces were used as received and dusted prior to use using a dry nitrogen stream. Surfaces modified with SAMs were formed by immersion of the surface in a solution nominally 1 mM in SAM concentration. Either ethanol or chloroform were used as solvents. Immersion times were at least 24 hours, followed by extensive rinsing with the neat solvent used during self-assembly. The samples were then allowed to dry in a dry box overnight prior to the contact angle measurements.

All other surfaces were used as received. After preparation and treatment, each sample was cut into several smaller pieces, some of which were used for the contact angle measurements, and some for coating with the PDA solution. To coat the substrates, mixtures of diacetylene monomer as prepared in Example 6 and DMPC (6:4) were weighed into vials and suspended in HEPES buffer (5 mM, pH=7.2) to produce a 1 mM solution. The solutions were then probe sonicated using a Model XL2020 probe sonicator (commercially available from Misonix, Inc.; Farmington, N.Y.) for 1 minute at a power setting of 5, and then placed into a 4° C. refrigerator overnight (~16 hours). The samples were filtered through a 1.2 μm syringe filter and a stirred solution was polymerized by irradiating the sample beneath a 254 nm UV lamp at a distance of 3 cm for 20 minutes, resulting in the observation of a blue color. Using a syringe, several spots (40 μl each) of the polymerized solutions were placed onto a series of substrates specified in Table 1. The solutions were allowed to dry at room temperature, and the resulting color of the spots was recorded.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments set forth herein and that such embodiments are presented by way of example only, with the scope of the invention intended to be limited only by the claims.

What is claimed is:

1. A colorimetric sensor for detecting an analyte, comprising:
   a receptor; and
   a polymerized composition comprising at least one compound of the formula

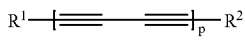

wherein $R^1$ comprises

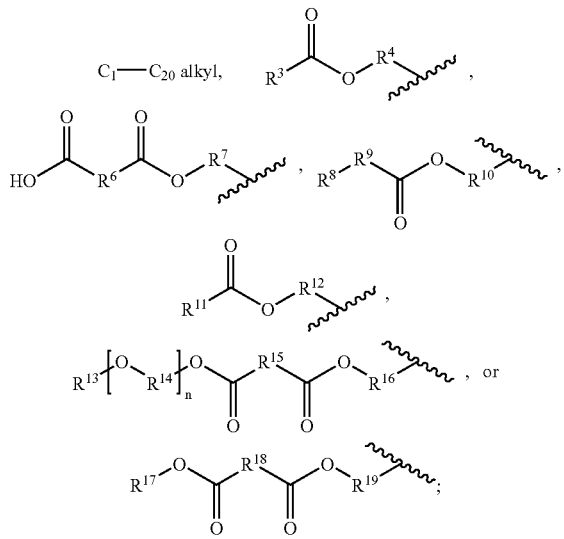

$R^2$ comprises

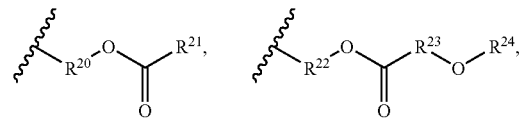

-continued

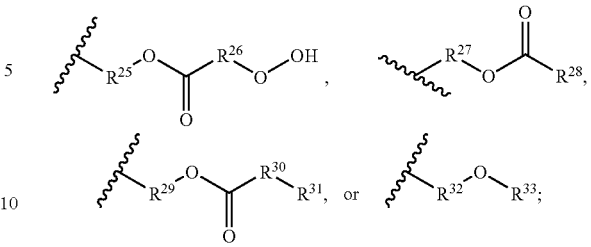

$R^3$, $R^8$, $R^{13}$, $R^{21}$, $R^{24}$, $R^{31}$ and $R^{33}$ are independently $C_1$-$C_{20}$ alkyl;

$R^4$, $R^7$, $R^{14}$, $R^{16}$, $R^{19}$, $R^{20}$, $R^{22}$, $R^{25}$, and $R^{32}$ are independently $C_1$-$C_{14}$ alkylene;

$R^6$, $R^{15}$, $R^{18}$, and $R^{26}$ are independently $C_1$-$C_{14}$ alkylene, $C_2$-$C_8$ alkenylene, or $C_6$-$C_{13}$ arylene;

$R^9$ is $C_1$-$C_{14}$ alkylene or —$NR^{34}$—;

$R^{10}$, $R^{12}$, $R^{27}$, and $R^{29}$ are independently $C_1$-$C_{14}$ alkylene or ($C_1$-$C_{14}$ alkylene)-($C_2$-$C_8$ arylene);

$R^{11}$ and $R^{28}$ are independently $C_2$-$C_{30}$ alkynyl;

$R^{17}$ is an ester-activating group;

$R^{23}$ is $C_6$-$C_{13}$ arylene;

$R^{30}$ is $C_1$-$C_{14}$ alkylene or —$NR^{36}$—;

$R^{34}$, and $R^{36}$ are $C_1$-$C_4$ alkyl;

p is 1-5;

n is 1-20;

wherein $R^1$ and $R^2$ are not the same;

wherein the receptor is incorporated into the polymerized composition to form a transducer; and wherein the transducer exhibits a color change when contacted with an analyte.

2. The sensor of claim 1, wherein $R^1$ is dodecyl or hexadecyl.

3. The sensor of claim 1, wherein $R^3$ is undecyl or pentadecyl.

4. The sensor of claim 1, wherein $R^{24}$ is methyl, ethyl, propyl, butyl, pentyl, hexyl, heptyl, octyl, nonyl, or dodecyl.

5. The sensor of claim 1, wherein $R^{33}$ is dodecyl, tetradecyl, hexadecyl, or octadecyl.

6. The sensor of claim 1, wherein $R^4$ is methylene, trimethylene, or tetramethylene.

7. The sensor of claim 1, wherein $R^7$, $R^{16}$, $R^{19}$, $R^{20}$ and $R^{25}$ are independently ethylene, trimethylene, tetramethylene, pentamethylene, hexamethylene, heptamethylene, octamethylene, or nonamethylene.

8. The sensor of claim 1, wherein $R^{20}$ is methylene, trimethylene, or tetramethylene.

9. The sensor of claim 1, wherein $R^{22}$ is ethylene, trimethylene, or tetramethylene.

10. The sensor of claim 1, wherein $R^{32}$ is ethylene, trimethylene, tetramethylene, pentamethylene, or hexamethylene.

11. The sensor of claim 1, wherein $R^6$, $R^{15}$, $R^{18}$, and $R^{26}$ are independently ethylene, trimethylene, ethenylene, or phenylene.

12. The sensor of claim 1, wherein $R^8$ and $R^{31}$ are independently $C_1$-$C_{14}$ alkyl.

13. The sensor of claim 12, wherein $R^8$ and $R^{31}$ are independently butyl, pentyl or hexyl.

14. The sensor of claim 1, wherein $R^9$ and $R^{30}$ are independently methylene, NH-, -N($CH_2CH_3$)-, or -N($CH_3$)-.

15. The sensor of claim 1, wherein $R^{10}$, $R^{12}$, $R^{27}$, and $R^{29}$ are independently methylene, ethylene, trimethylene, tetramethylene, -C(CH$_3$)2-, CH((CH$_2$)$_{1-4}$CH$_3$)-, or -CH$_2$-phenylene.

16. The sensor of claim 1, wherein $R^{11}$ and $R^{28}$ are independently C$_2$-C$_{30}$ alkynyl having at least two carbon-carbon triple bonds.

17. The sensor of claim 16, wherein $R^{11}$ and $R^{28}$ are independently -(CH$_2$)$_8$-C≡C-C≡C-(CH$_2$)$_9$CH$_3$, or -(CH$_2$)$_8$-C≡C-C≡C-(CH$_2$)$_{11}$CH$_3$.

18. The sensor of claim 1, wherein $R^{13}$ is C$_1$-C$_4$ alkyl.

19. The sensor of claim 1, wherein $R^{14}$ is C$_1$-C$_4$ alkylene.

20. The sensor of claim 1, wherein $R^{17}$ is 2,5-dioxo-1-pyrrolidinyl.

21. The sensor of claim 1, wherein $R^{23}$ is phenylene.

22. The sensor of claim 1, wherein n 3-17, 6-14, or 9-11.

23. The sensor of claim 1, wherein p is 1 or 2.

24. The sensor of claim 1 wherein $R^1$ is

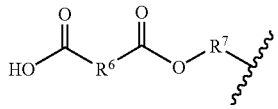

wherein $R^7$ is ethylene, trimethylene, tetramethylene, pentamethylene, hexamethylene, heptamethylene, octamethylene, or nonamethylene, and $R^6$ is ethylene, trimethylene, ethenylene, or phenylene; and
wherein $R^2$ is

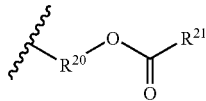

wherein $R^{20}$ is ethylene, trimethylene, tetramethylene, pentamethylene, hexamethylene, heptamethylene, octamethylene, or nonamethylene, and wherein $R^{21}$ is undecyl, tridecyl, pentadecyl, heptadecyl; and
wherein p is 1.

25. The sensor of claim 24, wherein $R^1$ is

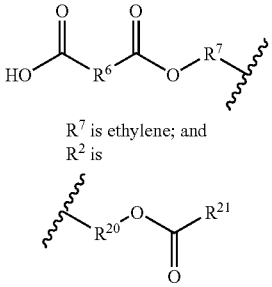

$R^7$ is ethylene; and
$R^2$ is $R^{20}$ is tetramethylene, and wherein $R^{21}$ is tridecyl; and
p is 1.

26. The sensor of claim 1, wherein the receptor is selected from the group consisting of phospholipid and glycerol.

27. The sensor of claim 1, wherein the transducer is dispersed in an aqueous solution.

28. The sensor of claim 1, wherein the transducer is coated on a substrate.

29. The sensor of claim 28, wherein the substrate exhibits a contact angle less than 50 degrees using methylene iodide.

30. The sensor of claim 29, wherein the substrate is selected from the group consisting of silica gel plate, paper, glass, textured photo paper, gloss photo paper, and microporous film.

31. The sensor of claim 1, wherein the receptor is incorporated into the polymerized composition by physical mixing.

32. The sensor of claim 1, wherein the receptor is incorporated into the polymerized composition by covalently binding the receptor to the polymerized composition.

* * * * *

UNITED STATES PATENT AND TRADEMARK OFFICE
CERTIFICATE OF CORRECTION

PATENT NO. : 7,364,918 B2  Page 1 of 3
APPLICATION NO. : 10/738573
DATED : April 29, 2008
INVENTOR(S) : Ryan B. Prince It is certified that error appears in the above-identified patent and that said Letters Patent is hereby corrected as shown below:

On the Title Page Item -56- on Page 2, under (Other Publications)
Line 6, delete "Monolayrs" and insert -- Monolayers --, therefor.
Line 24 delete "9-Decyn-1-ol";" and insert -- 9-Decyn-1-ol"; --, therefor.

On the Title Page Item -56- on Page 3, under (Other Publications)
Line 21, delete "Wafer" and insert -- Water --, therefor.

Figure 8:
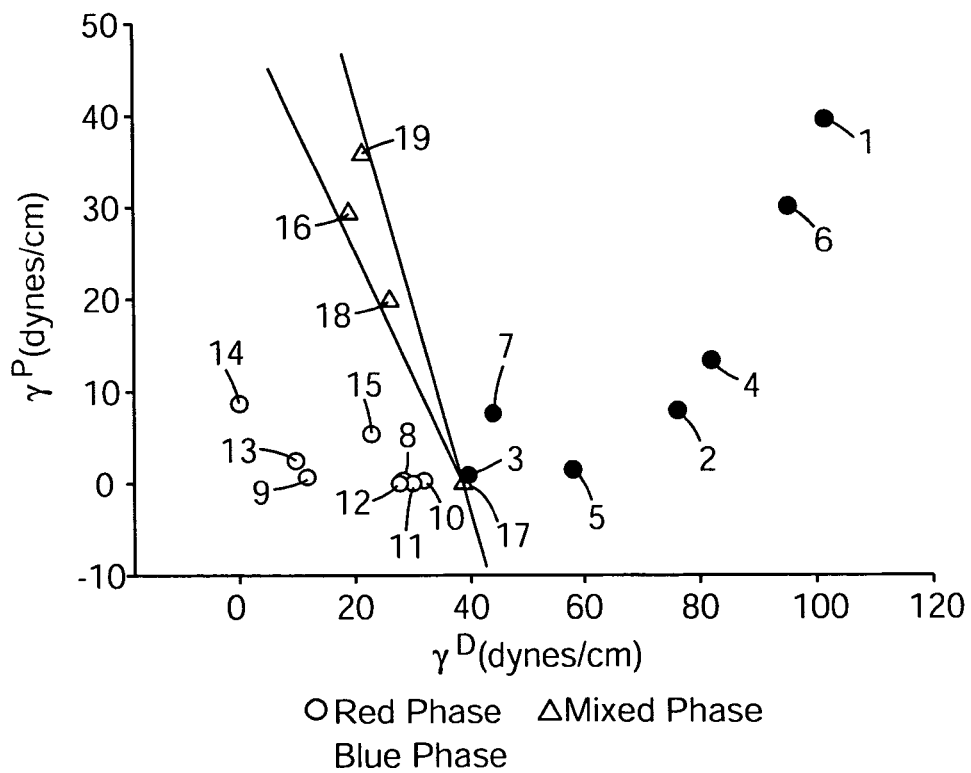
FIG. 8 is a phase diagram showing the colors of the coated and dried polydiacetylene film as a function of the surface tension of the substrate.

On Sheet 3 of 3 of the Drawings, in (Fig. 8)
Before "Blue Phase" insert -- ● --.

Column 4
Line 53, delete "sheroplasts," and insert -- spheroplasts, --, therefor.
Line 65, delete "Bilavers" and insert -- Bilayers --, therefor.
Line 66, delete "Membrances:" and insert -- Membranes; --, therefor.

Column 6
Line 7, delete "$C^6$-$C^{18}$" and insert -- $C_6$-$C_{18}$ --, therefor.
Line 33, delete "$CH_2CH_2CH_2CH_2CH_2CH_2$" and insert
 -- $CH_2CH_2CH_2CH_2CH_2CH_2CH_2$ --, therefor.
Line 39, delete "$C_1$-$C_{14}$" and insert -- $C_1$-$C_4$ --, therefor.
Lines 51-52, delete "$R_{10}$ when $R_{10}$" and insert -- $R^{10}$ when $R^{10}$ --, therefor.

Column 7
Line 24, delete "$CH_2CH_2CH_2CH_2CH_2CH_2$" and insert
 -- $CH_2CH_2CH_2CH_2CH_2CH_2CH_2$ --, therefor.
Line 51, delete "$CH_2CH_2CH_2CH_2CH_2CH_2$" and insert
 -- $CH_2CH_2CH_2CH_2CH_2CH_2CH_2$ --, therefor.
Line 61, delete "$CH_2CH_2CH_2CH_2CH_2CH_2$" and insert
 -- $CH_2CH_2CH_2CH_2CH_2CH_2CH_2$ --, therefor.

Column 8
Line 12, delete "$R_{25}$" and insert -- $R^{25}$ --, therefor.
Line 17, delete "$CH_2CH_2CH_2CH_2CH_2CH_2$" and insert
 -- $CH_2CH_2CH_2CH_2CH_2CH_2CH_2$ --, therefor.

UNITED STATES PATENT AND TRADEMARK OFFICE
CERTIFICATE OF CORRECTION

PATENT NO.        : 7,364,918 B2
APPLICATION NO.   : 10/738573
DATED             : April 29, 2008
INVENTOR(S)       : Ryan B. Prince It is certified that error appears in the above-identified patent and that said Letters Patent is hereby corrected as shown below:

Column 11
Line 49, delete "Phillipe;" and insert -- Philippe; --, therefor.

Column 12
Line 17, delete "leukocycte" and insert -- leukocyte --, therefor.
Lines 25-26, delete "Ophthaalmic" and insert -- Ophthalmic --, therefor.
Line 27, delete "leukocyctes" and insert -- leukocytes --, therefor.
Line 30, delete "H2O2" and insert -- $H_2O_2$ --, therefor.
Line 36, after "4,434,235" insert -- . --.

Column 20
Line 40, delete "2.2." and insert -- 2.2--, therefor.

Column 21
Line 3, delete "Preperation" and Insert -- Preparation --, therefor.

Column 22
Line 33, after "Table 5)" insert -- . --.

Column 30
Lines 3-7, in Claim 1, delete " 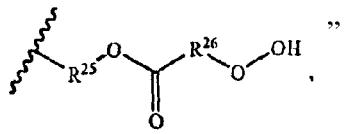 "

and insert -- 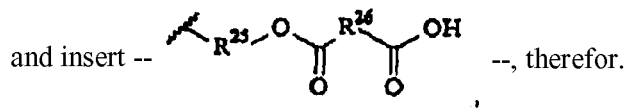 --, therefor.

Line 66, in Claim 14, delete "NH-," and insert -- -NH-, --, therefor.

UNITED STATES PATENT AND TRADEMARK OFFICE
CERTIFICATE OF CORRECTION

PATENT NO. : 7,364,918 B2
APPLICATION NO. : 10/738573
DATED : April 29, 2008
INVENTOR(S) : Ryan B. Prince It is certified that error appears in the above-identified patent and that said Letters Patent is hereby corrected as shown below:

Column 31
Line 3, in Claim 15, delete "-C(CH$_3$) 2-, CH((CH$_2$)$_{1-4}$" and insert
-- -C(CH$_3$)$_2$-, -CH((CH$_2$)$_{1-4}$ --, therefor.
Line 16, in Claim 22, after "n" insert -- is --.

Signed and Sealed this

Twenty-second Day of July, 2008

JON W. DUDAS
*Director of the United States Patent and Trademark Office*